(12) United States Patent
Rozenfeld

(10) Patent No.: US 9,767,559 B1
(45) Date of Patent: Sep. 19, 2017

(54) SYSTEM AND METHOD FOR RECONSTRUCTING SENSOR LOCATIONS IN RADIOGRAPHIC IMAGES

(71) Applicant: GIVEN IMAGING LTD., Yoqneam (IL)

(72) Inventor: Stas Rozenfeld, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 164 days.

(21) Appl. No.: 14/670,487

(22) Filed: Mar. 27, 2015

Related U.S. Application Data

(60) Provisional application No. 61/971,128, filed on Mar. 27, 2014.

(51) Int. Cl.
*G06T 7/00* (2017.01)
*A61B 6/00* (2006.01)

(52) U.S. Cl.
CPC .......... *G06T 7/0016* (2013.01); *A61B 6/4057* (2013.01); *A61B 6/4208* (2013.01); *A61B 6/52* (2013.01); *G06T 7/0038* (2013.01); *G06T 7/0044* (2013.01); *G06K 2209/057* (2013.01); *G06T 2207/10016* (2013.01); *G06T 2207/10124* (2013.01); *G06T 2207/30004* (2013.01)

(58) Field of Classification Search
CPC . G06T 2207/10116; G06T 2207/30204; G06T 2207/30021; G06T 2207/10072; G06T 2207/10016; G06T 2207/30004; G06T 2207/30052; G06T 7/0012; G06T 7/0016; G06F 19/3406; G06K 2209/057
See application file for complete search history.

(56) References Cited

U.S. PATENT DOCUMENTS

| | | | | |
|---|---|---|---|---|
| 2009/0257554 | A1* | 10/2009 | Parks | A61B 6/12 378/44 |
| 2011/0135176 | A1* | 6/2011 | Lendl | G06T 7/246 382/130 |
| 2012/0004537 | A1* | 1/2012 | Tolkowsky | A61B 5/066 600/424 |

* cited by examiner

*Primary Examiner* — Kenny Cese
(74) *Attorney, Agent, or Firm* — Pearl Cohen Zedek Latzer Baratz LLP

(57) ABSTRACT

A system and method for reconstructing locations of sensors in radiopaque images may estimate sensor locations in two groups of good radiographic images and use them to estimate candidate sensor locations in a group of bad radiographic images B1, . . . , Bn in which many sensors are indiscernible. A first iterative process pervading from the first image B1 to the last image Bn may determine a first set of candidate sensor locations, and a second iterative process pervading from the last image Bn to the first image B1 may determine a second set of candidate sensor location for each image. Location of a sensor in each image Bi may be estimated based on the pertinent first and second candidate sensor locations related, or determined for, the particular sensor in the particular image. Sensor locations still missing in the series of images are, then, estimated using the already estimated sensor locations.

23 Claims, 15 Drawing Sheets

US 9,767,559 B1

SYSTEM AND METHOD FOR RECONSTRUCTING SENSOR LOCATIONS IN RADIOGRAPHIC IMAGES

CROSS REFERENCE TO RELATED APPLICATION

The present application claims the benefit of prior U.S. provisional application No. 61/971,128 filed on Mar. 27, 2014, incorporated by reference herein in its entirety.

FIELD OF THE INVENTION

The present invention generally relates to an imaging system and more specifically to a method for spatiotemporally reconstructing or estimating the locations of sensors positioned in a body organ which is imaged, for example, radiographically, and to a system that uses the sensor locations reconstruction/estimation method for localizing such sensors.

BACKGROUND

A variety of medical imaging technologies is available for producing images of the interior of the human body, for example for diagnostic purpose. Radiography (an imaging technique that uses electromagnetic radiation other than visible light, for example X-rays, to view the internal structure of an object such as the human body) is frequently used for this purpose, and fluoroscopy is an imaging technique used by physicians/radiologists to obtain real-time moving image of internal organs or structures of a patient (e.g., small bowel, colon, anorectum, or other parts of the gastrointestinal (GI) system, blood vessel, etc.) through the use of a fluoroscope. Such images are typically used during surgery, for example, in order to ensure that a stent or screw is inserted correctly.

It is also known that a contrast material may be introduced into the patient to help mark anatomy parts as part of a study using fluoroscopic imaging. The contrast material may reveal functioning of, for example, blood vessels or the GI tract. Known contrast materials may include, for example, barium in the form of barium sulfate (BaSO4), which may be administered orally or rectally for GI tract evaluation, and iodine in various proprietary forms. These contrast materials absorb or scatter significant amounts of x-ray radiation and may be used with real time imaging to demonstrate dynamic bodily processes, for example esophageal peristalsis. (Esophageal peristalsis refers to the contraction of muscles in the esophagus to push forward food and liquids through the esophagus to the stomach.

There are conventional imaging systems, one of which is described in U.S. Patent Publication No. 2009/0257554, that use a contrast material to visualize and display body organs or structures, for example during operation. Sensors are often positioned in a body organ (e.g., by using a catheter) to be imaged in order to measure and display physiological parameters (e.g., peristaltic pressure) that pertain to the visualized body organ. In order to interpret the measurements correctly, which is a prerequisite to useful analysis, each measurement has to be associated with the correct sensor and with the correct sensor's location in images of the radiographically imaged organ. However, as the contrast (radiopaque) material moves in the body organ, for example in the esophagus (e.g., during a patient swallowing), it may occlude or hide one or more sensors partly, entirely, completely or to some extent, and thus render sensors radiographically invisible/indiscernible. The level of invisibility of sensors depends, among other things, on the density and propagation pattern of the contrast material in the body organ. That is, sensors may be indiscernible in some images, partly or fully discernible in other images, and very, or faintly discernible in other images.

SUMMARY

While using contrast material may be beneficial in imaging body organs, it would be beneficial to have a system and method that reliably reconstruct sensor locations in each radiographic image even though the contrast material may, at times, radiographically occlude some of the sensors, for example while it moves in the body organ.

Embodiments of the invention, which may be directed to estimation of locations of radiopaque sensors in radiographic images, may comprise using two groups of chronologically captured (e.g., ordered by time of capture) 'good' radiographic images, in which many sensors are discernible, detectable, or at least partially visible (for example by not being occluded or opacified by a contrast material), to determine candidate sensor locations in a group of n chronologically captured 'bad' images, B1, B2, ..., Bn, in which all or many sensors are indiscernible or not detectable in the image as sensors (for example due to the sensors being occluded or opacified by a contrast material). The images selected for the groups of good images and the group of bad images may be selected such that images in each group are mutually ordered chronologically (e.g., by using timestamps), and the group of bad images, as a whole, is chronologically interposed or placed between the two groups of 'good' images. A 'good' image may be an image that includes a number of radiographically discernible sensors that is equal to or greater than a threshold number/value. A 'bad' image may be an image that includes no radiographically discernible sensors at all, or a number of radiographically discernible sensors that is less or lower than a/the threshold number.

Embodiments of the invention may comprise using two iterative processes: (1) a first iterative process that 'pervades', or cascades, in one 'direction' (e.g. a direction in a series of images) from the first 'bad' image, B1, to the last 'bad' image, Bn, to determine a first set of candidate sensor locations ($S_{Ci}^{1}$) ('i' denotes bad image Bi) for each bad image Bi, and (2) a second iterative process that pervades, or cascades, in the opposite direction from the last 'bad' image, Bn, to the first 'bad' image, B1, to determine a second set of candidate sensor locations ($S_{Ci}^{2}$) in each bad image Bi. The first iterative process may be based on or commence using sensor locations that are estimated (e.g., reconstructed or determined) in the chronologically last image of the group of good images chronologically preceding the group of bad images. The second iterative process may be based on or commence using sensor locations that are estimated (e.g., reconstructed or determined) in the first good image following the group of bad images.

The actual location ($S_{L\_k}$) of a particular sensor (k) in a particular bad image, Bi, may be determined based on comparison of, or from, the pertinent first and second candidate sensor locations (e.g., $S_{CL\_k\_i}^{1}$ and $S_{CL\_k\_i}^{2}$) determined for the particular sensor in the particular bad image Bi. The comparison process may be done (e.g., it may be meaningful), for example, only if each of the two sets of candidate sensor locations determined or calculated for this particular Bi contains a candidate sensor location for this specific sensor (k). For example, a sensor location ($S_{L\_k}$)

estimated for a sensor k in a bad image Bi may be a function of a first candidate sensor location and a second candidate sensor location (e.g., $S_{CL\_k\_i}^1$ and $S_{CL\_k\_i}^2$, respectively) determined for the particular sensor (e.g., $S_L = f(S_L^1, S_L^2)$). For example, a location estimation $S_L$ of a sensor k in a bad image Bi may be determined to be either one of the two pertinent candidate sensor locations (e.g., $S_{CL\_k\_i}^1$ or $S_{CL\_k\_i}^2$), or a location that is derivable from these two candidate sensor locations. For example, location estimation $S_L$ of sensor k may be an average of the two pertinent candidate sensor locations, or a location in-between the two candidate sensor locations.

A first candidate sensor location and a second candidate sensor location determined for a particular sensor in a particular image Bi may be compared, and if the two candidate sensor locations are consistent (e.g., in agreement, overlap or coincide), within a predetermined margin, then the location of the particular sensor may be estimated from, or using, the compared, or consistent, candidate sensor locations. Two candidate sensor locations may be regarded as consistent or congruous if they have identical or similar coordinates in the image, or a distance (e.g., measured in number of pixels) between the two candidate sensor locations is less than a threshold value. If the two candidate sensor locations are not consistent/congruous, either candidate sensor location, or both candidate sensor locations, may not be eligible for estimating a sensor's location and, therefore, it/they may be discarded, or simply ignored.

An additional process comprising estimation of a location of a particular sensor in a particular image, may be performed with respect to already known location of other sensors in the same particular image, and/or with respect to already known locations of sensors in other images.

Location of sensors that are indiscernible and cannot be visually localized by themselves, may be determined by using a variety of methods. For example, locations of indiscernible sensors may be interpolated using locations of discernible sensors. Estimation of additional sensor locations may include estimation of individual sensor locations; that is, estimation of sensor locations may be performed on individual basis.

Some embodiments for reconstructing sensor locations from radiographic images may include radiographically imaging a body organ containing a plurality of (e.g., m) radiopaque sensors to provide a stream or series of images comprising a first and second groups of chronologically captured images, and a third group of chronologically captured images interposed between the first and second groups of images, each image of the first and second groups of images comprising a number of discernible sensors that is equal to or greater than a threshold number, each image of the third group of images comprising a number of discernible sensors that is less than the threshold number. These embodiments may also comprise a step of estimating sensor locations in images of the third group of images based on locations of sensors that are already estimated in an image of the first group of images and locations of sensors that are already estimated in an image of the second group of images, and also a step of estimating additional sensor locations in images of the stream/series of images based on the already determined locations of indiscernible sensors or based on the already reconstructed locations of discernible sensors, or based on both types of sensor locations.

Also disclosed herein is a system for estimating sensor locations from/in radiographic images. In some embodiments the system may include a computing device that may be configured to receive a series of chronologically captured radiographic images (e.g., ordered by time of image capture) imaging a body organ containing plurality (e.g., m) radiopaque sensors, the series of images may include a first and second groups of chronologically captured images including, each, a number of discernible sensors equal to or greater than a threshold number, and a third group of n chronologically captured images B1, B2, ..., Bn chronologically captured between the first and second groups of images, where each image of the third group of images may include a number of discernible sensors that is less than the threshold number. According to some embodiments the system may include, or further include, a sensor locations construction (SLC) unit that may be configured to, for example: (i) reconstruct locations of discernable sensors in the first and second groups of images (ii) use reconstructed discernible sensor locations in the first and second groups of images to reconstruct additional discernable sensor locations and determine sensor locations in these groups for indiscernible sensors, and, in addition, (iii) estimate sensor locations for both discernible and indiscernible sensors in images B1, B2, ..., Bn based on sensor locations that are discernible in a chronologically last image of the first group of images, and sensor locations that are discernible in a chronologically first image of the second group of images. The SLC unit may also be configured to improve the overall sensor location detection, or reconstruction, in the entire series of chronologically captured radiographic images. According to some embodiments the system may include, or further include, a display device to display images with discernible sensor locations and/or with reconstructed sensor locations.

BRIEF DESCRIPTION OF THE DRAWINGS

Various exemplary embodiments are illustrated in the accompanying figures with the intent that these examples not be restrictive. It will be appreciated that for simplicity and clarity of the illustration, elements shown in the figures referenced below are not necessarily drawn to scale. Also, where considered appropriate, reference numerals may be repeated among the figures to indicate like, corresponding or analogous elements. Of the accompanying figures.

DETAILED DESCRIPTION

Figure 1A:
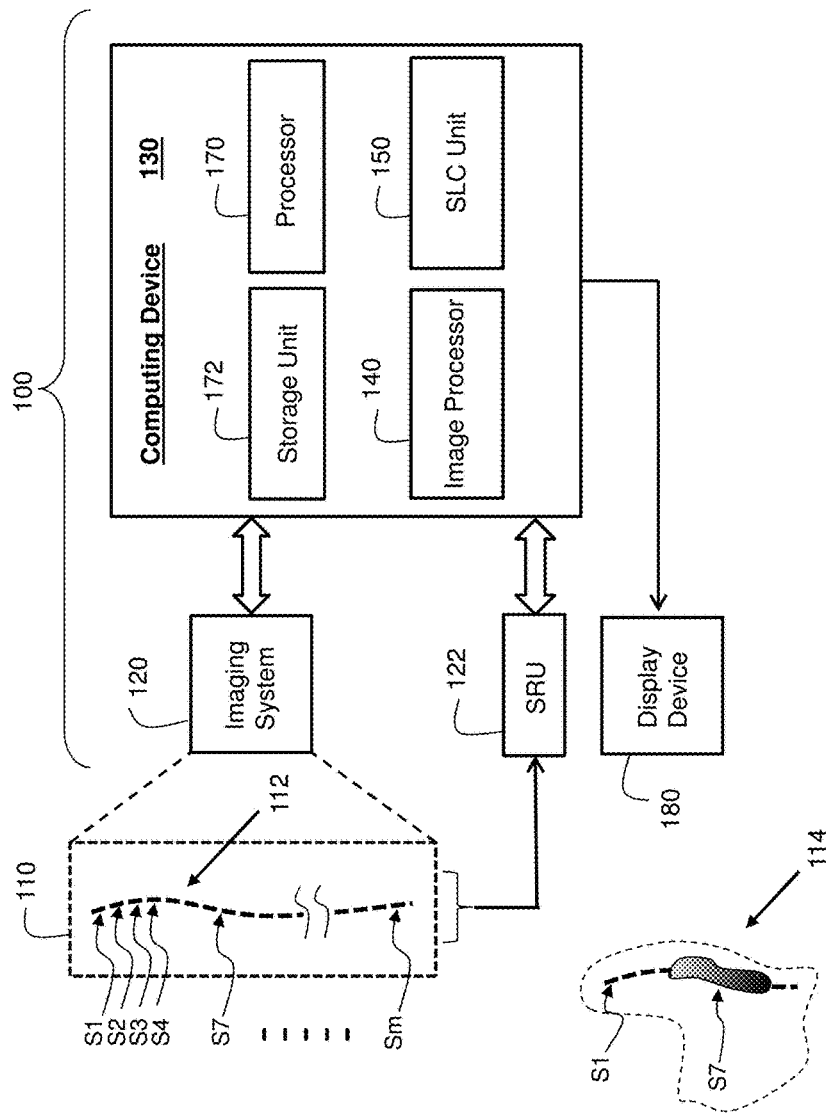
FIG. 1A is a block diagram of a radiographic imaging system for radiographically imaging a body organ according to an example embodiment.

The description that follows provides various details of exemplary embodiments. However, this description is not intended to limit the scope of the claims but instead to explain various principles of the invention and the manner of practicing it.

Although embodiments of the invention are not limited in this regard, discussions utilizing terms such as, for example, "processing", "computing", "calculating", "determining", "inferring", "deducing", "establishing", "analyzing", "checking", "estimating" or the like, may refer to operation(s) and/or process(es) of a computer, a computing platform, a computing system, or other electronic computing device, that manipulate and/or transform data represented as physical (e.g., electronic) quantities within the computer's registers and/or memories into other data similarly represented as physical quantities within the computer's registers and/or memories or other information non-transitory storage medium that may store instructions to perform operations and/or processes. Unless explicitly stated, the embodiments of methods described herein are not constrained to a particular order or sequence of steps, operations or procedures. Additionally, some of the described method embodiments, steps or elements thereof can occur or be performed simultaneously or concurrently, for example at the same point in time.

"Discernible" may refer to a sensor that is visible in an image. (Such sensors are relatively easily detectable by a processor using an algorithm.) "Indiscernible" may refer to a sensor that is invisible in an image. (Such sensors are usually undetectable by a processor, hence the use of sensor locations estimation methods disclosed herein.) "Reconstruction" of a sensor location may refer to, or include, a process by which a discernible sensor is detected in radiographic images, and its location in the image is defined using a coordinate system and, optionally, presented visually. "Determination" of a sensor location may refer to, or include, a process by which a location of an indiscernible sensor in an image is 'guessed' or inferred using other sensor locations (e.g., locations of discernible sensors and/or sensor locations determined for other indiscernible sensors). "Determination" is also used in the context of determination of a candidate sensor location. "Estimation" of a sensor location may refer to, or include, a process by which a location of a discernible sensor in an image is obtained through detection of the sensor in the image, and also a process by which a location of an indiscernible sensor in an image is 'guessed' using two candidate sensor locations.

The following notations are used herein: (i) $S_{CLi}^1$ and $S_{CLi}^2$, respectively, are or represent a first set of candidate sensor locations and a second set of candidate sensor locations that are estimated for sensor locations in a given bad image Bi (i=1, 2, ..., n), (ii) $S_{CL\_k\_i}^1$ is or represents a first candidate sensor location for sensor k in image Bi ($S_{CL\_k\_i}^1$ is an 'element' of set $S_{CLi}^1$), (iii) similarly, $S_{CL\_k\_i}^2$ is or represents a second candidate sensor location for sensor k in image Bi ($S_{CL\_k\_i}^2$ is an 'element' of set $S_{CLi}^2$), and (iii) $S_L$ is an estimation of a 'true' (genuine) location of a sensor in a radiographic image. When discussed herein a "location" of a sensor may be the location of an image of the sensor within an image (e.g. a radiographic image, a photographic image, an ultrasound image, or other image). Similarly, when discussed herein, a sensor may be an actual real-world sensor, or an image of a sensor within an image. Thus an "image comprising a sensor" may refer to an image including an image of a sensor.

Displaying a location of a (radiopaque) sensor in a radiographic image may mean or include estimating the location of the sensor in the image and altering the (original, or raw) image to include in it (e.g., by addition of) a graphical object (e.g., "+", "x", "o", or another shape, notation or symbol) whose positional location (e.g., coordinates) represents or indicates the location of the sensor in the image. Displaying a sensor's location may mean or include, for example, visually superimposing an image of, or that includes, a graphical object on the radiographic image in a way that the graphical object, while superimposed on the radiographic image, represents or indicates the location of the sensor in the radiographic image.

FIG. 1A is a block diagram of a visualization system 100 according to an example embodiment of the invention. Visualization system 100 may include an imaging system 120 for obtaining a series of successive radioscopic images of a region of interest (ROI) 110 in or of a patient's body, a sensors reading unit ("SRU") 122 for reading or measuring, or otherwise detecting sensor output values, a computing system or device 130 for receiving image data (and possibly other data) from imaging system 120 and sensors' information (e.g., identification information, output values) from SRU 122, and for processing the image data and the sensors information, and a display device 180 (e.g. a monitor) for displaying any of radioscopic images, estimated sensor locations and, optionally, sensors' output values (e.g., pressure values).

Before the radioscopic imaging/study/procedure is commenced, a sensing element 112 (e.g., a catheter with discrete sensors disposed thereon or therein) may be inserted into, and positioned or placed in, the body organ whose physiological functionality is to be studied or examined. Sensing element 112 may include m sensors, designated as S1, S2, ..., Sm. Sensors S1, S2, ..., Sm may be inserted into a body organ or portion in the ROI by using, for example, a catheter, or by using any other suitable method. When imaging system 120 images ROI 110, it also images all or some of the sensors of sensing element 112. For example, the number of sensors that are 'successfully' imaged (that is, clearly visible or discernible) in each image may vary from one image to another depending on for example, whether, or on the extent to which, the sensors are radiographically occluded by a contrast material that is administered into the body organ or portion and moves or flows, for example, by applied peristalsis, in ROI 110. (The contrast material may absorb or scatter significant amounts of x-ray radiation, and thus may be conspicuous radiographically.) Other reasons for sensors not being visible or discernable may occur. The body organ, portion or lumen may be or include, for example, the esophagus, a blood vessel, etc., in which m radiopaque sensors S1, S2, ..., Sm are disposed, distributed or placed.

Embodiments of the invention may include imaging the body organ or lumen and the m radiopaque sensors over time, for example such that a series of images are successively acquired one image at a time during a time period including one or more swallow procedures. Such imaging may be performed, for example, in order to provide a chronologically captured stream, or series, of radiopaque images (e.g., by outputting a signal or data representing these images) corresponding to one or more swallow procedures. With each swallow procedure may be associated a swallow sequence of images captured before, during and after a swallow of radiopaque (contrast) material. Embodiments of the methods described herein may be applied, for example, to each swallow sequence of images, as described herein.

The physical/actual spacing between sensors S1, S2 . . . , Sm, as well as the shape and dimensions of each sensor, may be known a priori and used to identify the sensors in radioscopic images. One or more sensors may be designed slightly differently than others in order for them to serve as fiducial indicia, or reference markers, in radioscopic images, in order to facilitate identification of sensors in radioscopic images. Special (e.g., dedicated) radio discernible markers may be built into the sensing device, or a radiographic 'signature' of certain non-sensing components of the sensing device may be used, to facilitate identification of the ordered sensors from images. Sensors S1, S2 . . . , Sm may be or include, for example, pressure sensors, pH sensors, temperature sensors, etc., or a combination of sensors of different types (e.g., pressure sensors and pH sensors).

Commercially available medical imaging system may be used to image a region of interest like or similar to ROI 110. Radio discernible sensors 112 may have any suitable size, shape, and material composition that may render them detectable by computing device 130 from radiographic images that are produced by imaging system 120. Imaging system 120 may image the ROI prior to the introduction of a contrast material to establish a baseline image. Once a suitable contrast material is introduced into ROI 110, imaging system 120 may acquire a series of images.

Computing device 130 may be of a type known in the art for processing medical image data, and it may interoperate with imaging system 120 to receive the series of successive radioscopic images for processing. Computing device 130 may be configured to perform steps of the methods disclosed herein, such as the image processing and display methods disclosed herein, by using computer-executable modules or instruction codes that may be stored, for example, in a storage unit 172, and executed by a suitable controller/processor (e.g., controller/processor 170). For example, processing units such as controller/processor 170, image processor 140, sensor locations construction ("SLC") unit 150, sensors reading unit ("SRU") 122, etc. may be configured to perform methods disclosed herein by, for example, executing code or software and/or including dedicated circuitry. Processors and units such as 170, 140, 150, 122 etc., may be or may be part of a computing system. SLC unit 150, or only functions thereof, may be embedded in or performed by controller/processor 170. Computing device 130 may also include image processor 140 and SLC unit 150. Image processor 140 may process radioscopic image data that it receives from imaging system 120, for example, to identify the body lumen or organ. SLC unit 150, possibly in conjunction with processor 140, may process the radioscopic image data, for example, to detect and identify sensors, or sensor locations S1, S2, . . . , Sm (or some of them) in each radioscopic image, and, if required, to estimate, and optionally display, locations for sensors (indiscernible or discernible, or sensors of both types) in one or more images.

Sensor Outputs Reading, and Association of Output Values with Imaged Sensors

Sensors reading unit (SRU) 122, which may be integrated into computing device 130, for example as interface module, may be configured to read or measure, or otherwise detect, the output values of sensors S1, S2, . . . , Sm serially or in parallel. Since detection of sensor outputs is faster than the imaging process, the output of the sensors may be detected, for any image, in series, one sensor output after another. SRU 122 may transfer the sensor output readings (values) to computing device 130, and computing device 130, by using, for example, processor 170, may respectively associate the sensors' output values with the sensor locations estimated by SLC unit 150, in the related image. If SLC unit 150 cannot, or does not, identify a sensor in an image, it may infer its location in the image from identified locations of other sensors and/or from sensors identified in previous or subsequent images when multiple images are processed, such as in a video stream, and computing device 130 may handle 'inferred' sensor locations as if they were identified; i.e., in the same way as it handles identified sensors.

By using the information transferred from SRU 122 (e.g., sensors' identification codes, sensors' output values, etc.), computing device 130 may 'know' which sensor that computing device 130 identifies in the image is the first sensor (e.g., topmost in the image, or leftmost in in the image, etc.), the second sensor, and so on, and which measured output value is associated with (read/measured from) which sensor. SRU 122 may be a separate apparatus or a component thereof or embedded in computing device 130.

Estimating Locations of Indiscernible Sensors

As explained herein, one or more sensors of sensing element 112, which may be positioned in the body organ that is imaged or that is to be imaged, may not be identifiable or detectable in a radioscopic image, for example due to it/them being radiographically indiscernible because it/they is/are 'hidden' (e.g., occluded, opacified or overlapped) by the radiographic contrast material, or because of a different reason. If SLC unit 150 cannot identify a particular sensor because it is occluded or opacified (e.g., sensor S7 is at 114, though indiscernible), it may estimate, deduct or infer the location of the sensor (e.g., sensor S7) using any of the methods disclosed herein.

Based on a priori information related to sensing element 112, such as the number and size of the sensors and the spacing between them, SLC unit 150 may reconstruct discernible sensor locations and estimate, determine or calculate, the 'expected' location(s) (e.g., coordinates) of the unidentified/indiscernible sensors or sensor locations.

SRU 122 and SLC unit 150 may be implemented in software or in hardware, or partly in hardware and partly in software: they may be dedicated hardware unit, or they may be a code or instructions executed by a controller/processor, e.g., image processor 140 or processor 170. The code/instructions may be distributed among two or more processors. For example, processor 170, by executing suitable software, code or instructions, may carry out steps which are performed by SRU 122 and SLC unit 150, and other functions in computing device 130, and thus may function as these units. Every process or method step described herein, or some of them, may be performed solely by sensor locations construction (SLC) unit (e.g., module, circuit) 150 or processor 170, or jointly by SLC 150 and processor 170. In places where it is stated that a controller or processor performs a process and/or method steps, the process and/or method steps may be performed by SLC unit 150, which may be a dedicated electrical module or circuit.

Figure 1B:
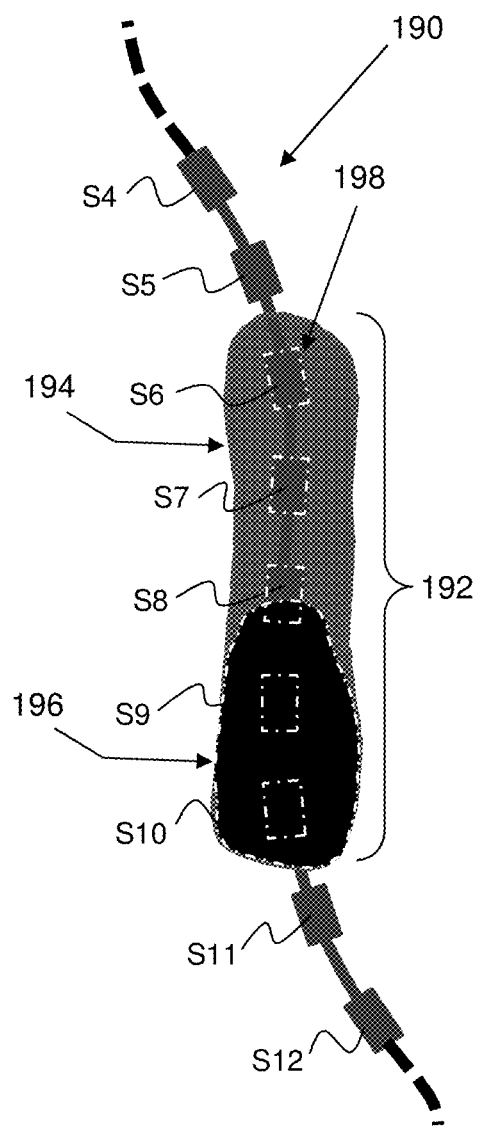
FIG. 1B depicts an example of distribution of radiographic contrast material in a body organ along a sensing element during a swallow according to an example embodiment.

FIG. 1B illustrates an example distribution of radiographic contrast material 192 along a sensing element 190 during swallow of a contrast material according to an example embodiment of the invention. A sensing element 190 may include m sensors (e.g., m>12), only nine of which are shown in FIG. 1B as an example, that is, sensors S4 through S12. Discernibility of a sensor in a radiographic image depends, among other things, on characteristics of the sensor and on the density of the contrast material interposed or placed between the sensor and the radiographic energy source.

A sensor may be 'very', or fully, discernible if the density of the contrast material is non-existent or negligible. The sensor may be discernible to some extent if the contrast material is dense to some extent, and indiscernible if the contrast material is very dense. By way of example, radiographic contrast 192 is shown having two, visually discernible, density regions, one of which is density region 194 and the other is density region 196. Contrast material 192 is denser in density region 196 than in density region 194, therefore density region 196 is darker ('more' black) than density region 194.

Sensors S4, S5, S11 and S12 are very discernible because they are not occluded at all by contrast material 192. Sensors S6 and S7 are partly discernible (e.g., less discernible than; e.g., sensors S4 and S5) because they are occluded by semitransparent region 194 of contrast material 192. Sensors S9 and S10 are indiscernible at all because they are completely occluded/opacified by completely opaque region 196 (of contrast material 192), which more dense than region 194 of contrast material 192. Part of sensor S8 is discernible in a similar way as sensors S6 and S7, and the other part of sensor S8 is indiscernible at all, as are sensors S9 and S10. (Sensors partly occluded by contrast material region 194 are made visually conspicuous, or accentuated, using a white, broken-lined, rectangle 198. Similarly, since sensors S9-S10 are completely indiscernible, their expected or 'guessed' locations are shown using white, broken-lined, rectangles.)

Figure 2A:
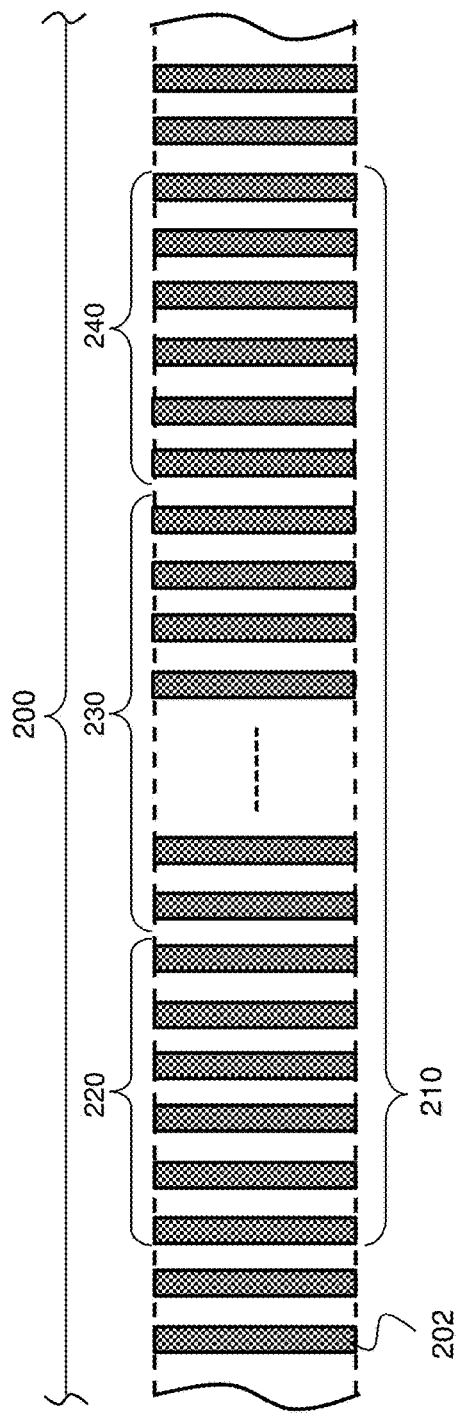
FIG. 2A schematically illustrates a stream of radiographic images acquired for a plurality of swallow sequences according to an example embodiment.

FIG. 2A schematically illustrates/shows a series 200 of chronologically captured radioscopic images (e.g., ordered by time of capture), with radioscopic image 202 being one image. The description related to FIG. 2A and to other drawings mentions the esophagus, so the contrast material is administered by swallowing. However, the esophagus is only an example body organ. A catheter with radiopaque sensors may be positioned in other body parts/lumens, for example in a blood vessel, and other contrast material administration methods may be used, which are suited for the imaged body organ/lumen.

Image series 210, which may refer to an example swallow procedure, comprises a first group or subseries of images (group 220) captured before the contrast material is administered to the body organ, a second group or subseries of images (group 230) captured while the contrast material moves in the body organ, and a third group or subseries of images (group 240) captured after the contrast material is diffused or cleared from the body organ.

Series 200 of radioscopic images may include images related to one swallow of contrast material or to multiple such swallows. Series 200 may be arranged chronologically by time of capture. The methods disclosed herein are applicable to individual swallows (e.g., individual times a patient swallows). For example, chronologically captured images related to one swallow procedure are shown at 210. Monitoring an individual swallow (e.g., by a system similar to system 100 of FIG. 1A) may result in or include obtaining a pre-swallow (contrast material free) series of chronologically captured radiographic images 220, then obtaining a second series of chronologically captured images 230 during which a contrast material is administered (e.g., swallowed) and moves in or through the body organ (and the series of radiographic images are obtained while the contrast material is moving (e.g., in the esophagus)), then (after emptying of, or clearing, the contrast material from the body organ) obtaining a third contrast material free series of chronologically captured radiographic images 240. (A sensing element identical or similar to, for example, sensing elements 112 of FIG. 1A is disposed or positioned in the body organ (e.g., esophagus) when images 210 are taken one image at a time.)

Image series 220 and 240 may respectively provide two groups of chronologically ordered 'good' radiographic images 250 and 270. An image regarded or classified as a 'good' radiographic image is a radiographic image in which all, most or many of the sensors are radiographically discernible; e.g., their locations clearly appear or detectable in the radiographic images. (Image series 250 may be, for example, a subseries of image series 220, and image series 270 may be, for example, a subseries of image series 240.)

Image series 230 may provide a group of chronologically ordered 'bad' radiographic images 260. (Image group 260 may be, for example, a subseries of image series 230.) An image regarded or classified as a 'bad' radiographic image is a radiographic image in which all, most or many of the sensors are indiscernible, for example, at all, or they are discernible poorly such that their location cannot be determined at all or reliably. (Group 260 of bad images may be chronologically interposed between group 250 of good images and group 270 of good images.)

Image series 220 and 240 may enable, for example, a controller/processor, such as processor 170 of FIG. 1A to detect, identify or single out an individual swallow (swallow procedure) and, in addition, the processor may use image groups 250 and 270 of good images, which it may respectively extract or select from image series 220 and 240, to determine sensor locations in bad images 260. 'Determining a sensor location' generally refers to, or uses, a process by which a location of an indiscernible sensor, for example in a bad image, is estimated, and the image subject of the sensor location estimation process is modified or altered such that it visualizes also the sensor's estimated location (e.g., by superimposing a graphical object that indicates the sensor's estimated location on the image).

Figure 2B:
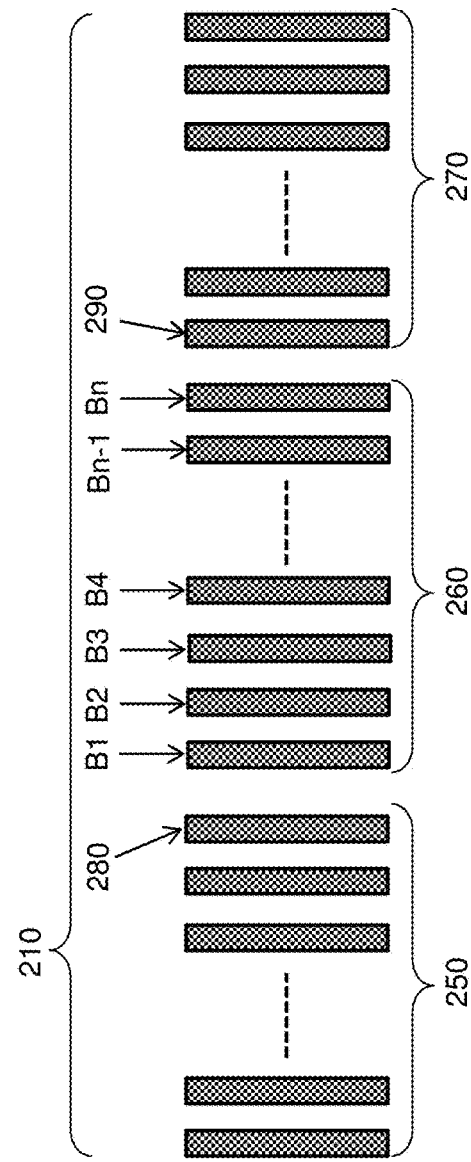
FIG. 2B schematically illustrates a swallow sequence according to an example embodiment.

FIG. 2B schematically illustrates/shows groups of good and bad images of a single swallow according to an example embodiment of the present invention. After sub-series 210 of images, which is related to an individual swallow, is identified within series 200 of radiographic images, images 210 undergoes the sensor location estimation methods disclosed herein. Initially, a quality criterion may be used in order to classify each image in sub-series 210 as a good image or as a bad image. As described herein, while images taken/captured during monitoring phases 220 and 240 are characterized by providing more good images than bad images, images taken/captured during monitoring phase 230 are characterized by providing more bad images than good images.

Good images and bad images may be grouped chronologically; namely, according to the order in which the images were taken, captured, generated or provided by/from a system similar to system 100 of FIG. 1. Referring to FIG. 2A, good images obtained during monitoring phase 220 may be grouped into a first group 250 of good images; bad images obtained during monitoring phase 230 may be grouped into a group 260 of bad images, and good images obtained during monitoring phase 240 may be grouped into a second group 270 of good images.

Each bad image, B, of group 260 of a number n of bad images may be indexed (Bi, i=1, 2, ..., n) according to the chronological order in which the images were taken, captured, generated or obtained. For example, a first bad image in group 260 may be indexed B1, as shown in FIG. 2B; the next (chronologically contiguous) bad image may be indexed B2, and so on, where the last bad image in group 260 may be indexed Bn, as shown in FIG. 2B. Indexing of the bad images may be performed in the order described herein, for example as described above. However, the bad images may be indexed in reverse order.

Reference numerals 280 and 290 respectively denote a chronologically last good image of group 250 of good images and a chronologically first good image of group 270 of good images. Good images 280 and 290 are chronologically contiguous to group 260 of bad images, though to opposite sides/ends of group 260. (Last good image 280 of group 250 of good images may be referred to as an 'edge good image' of group 250; first good image 290 of group 270 of good images may be referred to as an 'edge good image' of group 270.) For example, edge good image 280 is chronologically contiguous or adjacent to a first, chronologically captured, image of group 260 of bad images (for example to first bad image B1), and edge good image 290 is chronologically contiguous or adjacent to a last, chronologically captured, image of group 260 of bad images (for example to last bad image Bn). Bad image B1, the first bad image of bad image group 260, is chronologically captured or obtained after image 280. Bad image Bn, the last bad image of bad image group 260, is chronologically captured or obtained after good image 280 and before good image 290.

Sensor information related to, for example, sensor locations and/or sensor orientations, which may be obtained from good image 280 (the last good image chronologically preceding the group of bad images), may be used to enable, improve or enhance estimation or detection of sensor locations in bad image B1. (It is assumed that the sensor locations, or at least some of them, do not change significantly between chronologically contiguous images; e.g., between images 280 and B1, between images B1 and B2, and so on. In general, the higher the image capturing rate, the smaller the differences in sensor locations across chronologically contiguous images.) Then, sensor information calculated for, or derived from or in relation to, bad image B1 may be used to enable, improve or enhance estimation or detection of sensor locations in bad image B2, and so on; namely, this process may 'pervade', or 'propagate', iteratively from a good image to a bad image, and, then, from one bad image to another (e.g., from bad image Bi to the next bad image $B_{i+1}$), until sensor locations are estimates for each bad image Bi (i=1, 2, 3, ..., n). The sensor locations calculated for each bad image may be rechecked for consistency, or congruency, by performing the opposite process; that is, by using a similar process in a chronologically reversed order, that is, for bad image Bi, where i=n, n−1, n−2, ..., 1. That is, sensor information obtained from good image 290 (the first good image chronologically following the group of bad images) may be used to enable, improve or enhance estimation or detection of sensor locations in bad image Bn. Then, sensor information calculated for bad image Bn may be used to enable, improve or enhance estimation or detection of sensor locations in bad image $B_{n-1}$, and so on; namely, this process may 'pervade', 'propagate' or cascade iteratively in the opposite direction, that is, from bad image Bi to the chronologically preceding bad image $B_{i-1}$, until sensor locations are estimated, or calculated, for each bad image Bi (i=n, n−1, n−2, ..., 1).

Sensor locations estimated or determined (e.g., by calculation) for a particular bad image Bi (e.g., B7), for example by using sensor locations information that was obtained from the preceding bad image $B_{i-1}$ (e.g., B6) during the first iterative process, may respectively be compared to sensor locations that were estimated for the same bad image Bi by using sensor locations information that was obtained from the following/subsequent bad image $B_{i+1}$ (e.g., B8) during the second, or reversed/'backwards', iterative process. The comparison results, which may be, for example, consistency/congruency grades, may enable to respectively determine consistency, or congruency, between sensor locations that were estimated in the first iterative process, and sensor locations that were estimated in the second/reversed iterative process. A location estimated for a sensor by using any of the above-described iteration processes is referred to herein as a 'candidate sensor location'. A candidate sensor location obtained for a sensor k in bad image Bi by using a first iteration process (e.g., candidate sensor location $S_{CL\_k\_i}^{1}$) and another, nearby, candidate sensor location obtained for sensor k in bad image Bi by using a second (i.e., opposite, or reversed) iteration process (e.g., candidate sensor location $S_{CL\_k\_i}^{2}$) may form a pair of candidate sensor locations for sensor k in image Bi; e.g., locations pair $\{S_{CL\_k\_i}^{1}, S_{CL\_k\_i}^{2}\}$, from which the true location of a sensor, $(S_L)$, in image Bi may be determined or calculated.

Sensor locations in each bad image, Bi, may individually be estimated according to, depending on, or using the resulting candidate sensor locations. For example, if a candidate sensor location $S_{CL\_K\_i}^{1}$, which is estimated for a particular sensor $S_k$ in a particular bad image Bi from or by using a chronologically preceding image $B_{i-1}$, is location wise congruent, consistent or in agreement, within a predetermined margin, with a candidate sensor location $S_{CL\_K\_i}^{2}$, which is determined for the same particular sensor $S_k$ in the same particular bad image Bi from or by using a chronologically subsequent image $B_{i+1}$, this means that either the candidate sensor location $S_{CL\_K\_i}^{1}$ or the candidate sensor location $S_{CL\_K\_i}^{2}$, or a sensor location associated with or derivable from these two (from this pair of) candidate sensor locations represents, with high probability, the true (genuine) location of sensor $S_k$ in the radioscopic image Bi. In this example, the estimated sensor location may be, for example, graphically added to the image for displaying it (e.g., alone or with other, like-determined, sensor locations) to a user (e.g., physician, technician). However, if no consistency/congruency can be found between a candidate sensor location found for image Bi by or using the preceding image Bi−1 and a candidate sensor location found for image Bi by or using the subsequent image Bi+1, or vice versa, then either candidate sensor location, or both candidate sensor locations, may not be eligible for determining a sensor's location and, therefore, this candidate sensor location, or the two candidate sensor locations may be discarded, or simply ignored. If no consistency/congruency can be found between two candidate sensor locations that are related to the location of sensor $S_k$ in bad image Bi, the location of sensor $S_k$ in bad image Bi may have to be found (e.g., calculated/estimated) by using other methods. For example, it may be interpolated, for example, from sensor locations in bad image Bi which are successfully detected either because they are radiographically discernible, or as a result of the sensor location estimation process disclosed herein (e.g., application of the first iterative process and the second (the 'opposite', or reversed) iterative process and the comparison of their results).

Consistency, or congruency, between candidate sensor locations that are estimated for bad images may be checked, or determined on individual basis, that is, per sensor per image. A consistency grade or value, or a congruency grade or value, may be determined (e.g., calculated), for example by a controller or processor, for a pair of candidate sensor locations related to a particular sensor in a particular image independently of the location estimations related to the other sensors in this image and to sensors in other images. The controller, or processor may use the consistency grade to determine whether two candidate sensor locations associated with a particular sensor are consistent. If they are consistent, the controller or processor may use any of the candidate sensor locations, or both candidate sensor locations, to determine/calculate the location of the sensor for which the two candidate sensor locations were estimated.

Turning back to FIG. 1A, SLC unit 150 may, for example, determine a first set of candidate sensor location in image B1 for sensors in image B1 by using sensor locations estimated in an image (e.g., last chronologically captured image) of the first group of images (e.g., image 280 of the images group 250). SLC unit 150 may, then, use a first iterative process to iteratively determine, in or for each image Bi+1, a first set of candidate sensor locations corresponding to sensors in image Bi+1 from the first set of candidate sensor locations of preceding image Bi. Then, or concurrently, SLC unit 150 may determine a second set of candidate sensor location for sensors in image Bn by using sensor locations estimated in an image (e.g., first chronologically captured image) of the second group of images (e.g., image 290 of the images group 270). SLC unit 150 may, then, use a second iterative process to iteratively determine a second set of candidate sensor locations corresponding to sensors in image Bi−1 from the second set of candidate sensor locations of subsequent image Bi, Then, SLC unit 150 may compare, for each particular sensor Sk in each particular image Bi, the pertinent first candidate sensor location estimated during the first iterative process with the pertinent second candidate sensor location calculated during the second iterative process, and determine a sensor location for the particular sensor Sk in the particular image Bi by using the pertinent candidate sensor locations.

SLC unit 150 may determine the sensor location of/for the sensor Sk in a particular image Bi if the pertinent first and second candidate sensor locations obtained from the two iterative processes for the location of sensor Sk are spatially consistent, or in agreement, within a predefined margin. (The first and second iterative processes are described more fully herein.) Otherwise (the two candidate sensor locations are not consistent or do not exist), the location of sensor Sk it may be interpolated, for example, from sensor locations in image Bi which are successfully detected either because they are radiographically discernible, or as a result of the application of the first iterative process and the second (the 'opposite', or reversed) iterative process. All or some of the method steps described below, for example, in connection with FIG. 2C, FIGS. 3A-3B and FIG. 4 may be performed by SLC unit 150, and some or all of the description below related to FIGS. 5A-5H may describe operations executed by SLC unit 150.

Figure 2C:
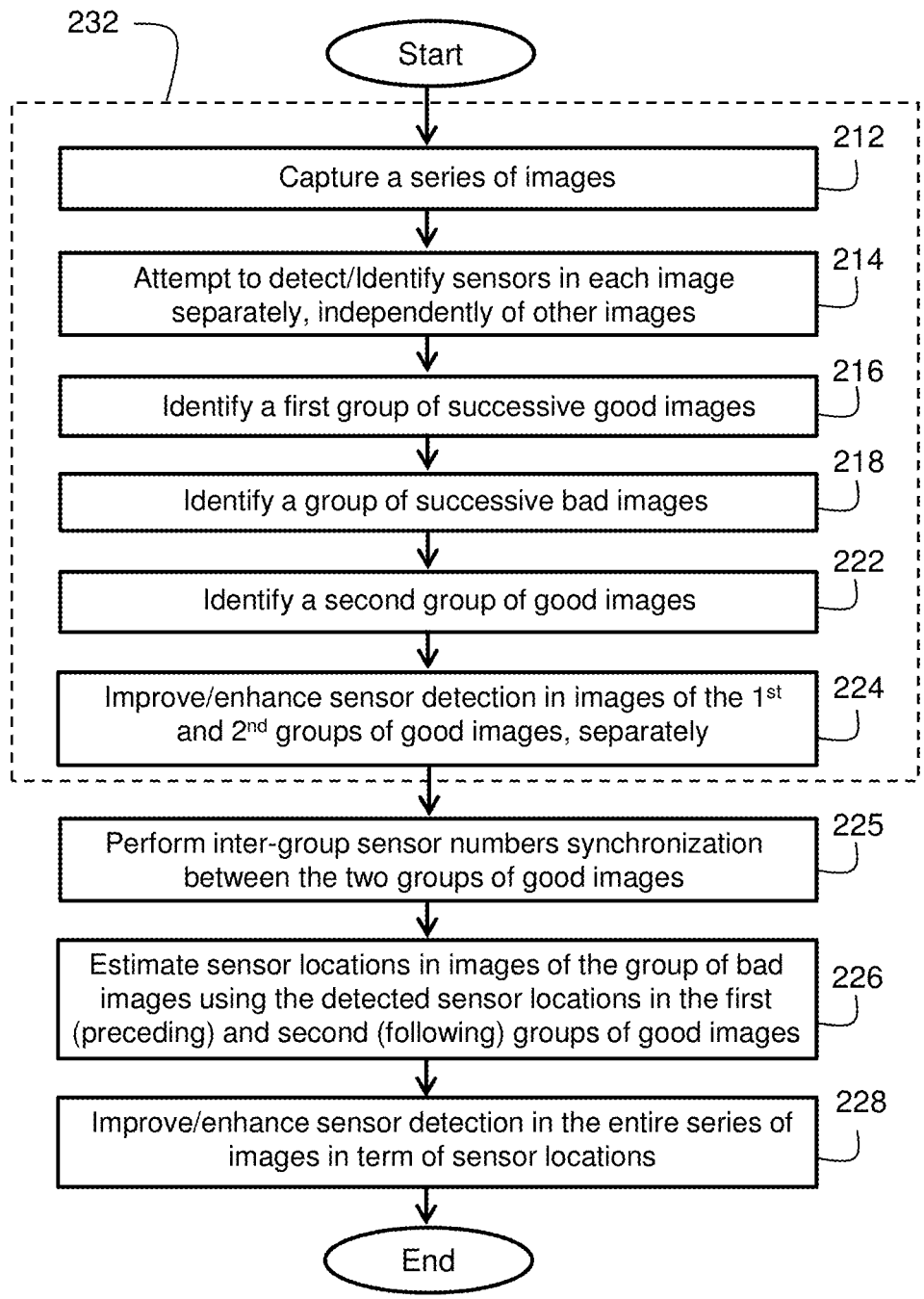
FIG. 2C shows a method for reconstructing sensor locations for radiopaque sensors in radiographic images related to a single swallow according to an example embodiment.

FIG. 2C shows a method for estimating sensor locations in a series of radiographic images of or relating to, for example, a swallow according to an example embodiment. FIG. 2C is described in association with FIGS. 2A-2B. At step 212, a controller may capture, receive or obtain a series of images such as series 200, where some images (e.g., images 220) may be taken/captured before a radiographic contrast material is swallowed, some other images (e.g., images 230) may be taken/captured during a swallow of a radiographic contrast material, and some other images (e.g., images 240) may be taken/captured after a contrast material is swallowed. (In other embodiments or applications the radiographic contrast material may be administered in ways other than swallowing, for example, to meet a need; e.g., to suit the body organ being imaged.)

At step 214, the controller may identify or detect sensors (sensor locations) in each image of the series of images separately, for example, in order to classify each image as good image or as bad image. The controller may independently serially number the detected sensors from 1 to q in different images, where q is a number of sensors actually identified/detected in an image. Depending on the radiographic conspicuousness of sensors in the images (for example), the value of q may change between images. For example, q may be equal to, say, 9, as demonstrated in image 540 in FIG. 5B, to 13, as demonstrated in image 550 in FIG. 5B, to 12, as demonstrated in image 560 in FIG. 5B, etc.

As described herein, the classification of an image to good image or to bad image may be based on the number of discernible sensors (q) that a processor can detect in the image, as opposed to estimating or interpolating sensor locations. A (classification) threshold value/number may be used to distinguish between good images and bad images. By way of example, FIG. 5B depicts images 540, 550, 560 and 570 with detected (discernible) sensor locations 542, 552, 562 and 572, respectively. Continuing the example, the detected (discernible) sensor locations in image 540 may initially be serially numbered 1 to 9 (q=9); the detected (discernible) sensor locations in image 550 may be initially serially numbered 1 to 13 (q=13); the detected (discernible) sensor locations in image 560 are initially numbered 1 to 12 (q=12), and the detected (discernible) sensor locations in image 570 may initially serially numbered 1 to 13 (q=13). (Assigning initial serial numbers to, or indexing, sensors in an image independently of other images, may result in a problem that a same particular sensor, or a particular sensor location, may be denoted by or assigned different index numbers in different images.)

At step 216, the controller may identify or form a first group of chronologically successive good images (e.g., group 250). (Such images are usually captured/taken before the radiographic contrast material is swallowed.) To solve the sensors' indexing problem described above (that a same sensor may be denoted by or assigned different numbers in different images), step 216 may include an intra-group synchronization step to synchronize the indexing, or numbering, between sensor locations within the first group of good images. (Synchronizing an indexed/numbered sensor location in an image may include serially renumbering the sensor location.)

At step 218, the controller may identify a group of chronologically successive bad images (e.g., group 260). (Such images are usually captured/taken during swallow of the radiographic contrast material.) At step 222, the controller may identify a second group of chronologically successive good images (e.g., group 270). (Such images are usually captured/taken after the radiographic contrast material is cleared.) As in, or as for, step 216, to solve the sensors' indexing problem described above, step 222 may include an intra-group synchronization step to synchronize the indexing, or numbering, between sensor locations within the second group of good images.

At step 224, the controller may independently and separately improve/enhance sensor detection in images in each of the first and second groups of good images in term of sensor locations. That is, already reconstructed sensor locations of clearly discernible sensors in images in the first group of good images may be used to estimate the location of other sensors in the same (first) group of good images. Similarly, already reconstructed sensor locations of clearly discernible sensors in images in the second group of good images may be used to estimate the location of other sensors in the second group of good images. By way of example, FIG. 5D depicts good image 540, which is improved or enhanced by using sensor locations 554 in good image 550. (Good images 540 and 550 belong to the same group 510 of good images.)

At step 224, the controller may also estimate sensor locations and/or improve, adjust or modify sensor locations in bad images in the group of bad images that are adjacent to one or more good images of either one of the two groups of good images. The controller may estimate and/or improve, adjust or modify sensor locations in bad images by using, or based on, sensor information that is related to or represents sensor locations in the adjacent good images. The controller may do this, for example, based on similarity, or resemblance, of visual sensor appearance in the adjacent frames. By way of example, FIG. 5E ("Enlarging segments") depicts a bad image (bad image 584) with seven sensor locations (sensor locations 1-7, shown at 586) that were determined by using the process described herein (e.g., above).

After a bad image is processed by using the methods described herein (e.g., to determine (additional) sensor locations in it based on sensor locations and similar appearances in an adjacent good image), the bad image may be deleted from the group of bad images and added to the adjacent group of good images. This way, the group of bad images, which forms, or is referred to herein as, a 'gap' in the stream of images, narrows down. By way of example, in FIG. 5E bad image 584 is removed/deleted from group 520 of bad images, thus narrowing group 520 from three bad images (images 580, 582, 584) to two bad images (images 580, 582), and added to group 530 of good images, thus extending group 530 from two good images (images 560, 570) to three good images (images 560, 570, 584). The controller may repeat the process iteratively until the two groups of good images 'meet' (by extending them towards one another), in which case the images gap is zeroed. In some cases, the sensor information obtained during the gap closing process may not suffice to zero the gap, so some images may still remain bad images after the process is completed/terminated.

At step 225, the controller may perform inter-group sensor numbers synchronization or adjustment between the first and second groups of good images so that each particular sensor, or its location in the images, is assigned the same indexing/serial number in images of the first and second groups of good images. The controller may serially renumber sensor locations in one or more images in the first group of good images, or in the second group of images, or in both groups during, or as part of, the sensor numbers synchronization/adjustment process.

After the controller adjusts (e.g., synchronizes) the indexing, or the numbers of the sensors locations in the corresponding images, the controller may, at step 226, estimate sensor locations in images of the group of bad images by using sensor locations detected in the first, chronologically preceding, group of good images, and in the second, chronologically subsequent, group of good images. The controller may perform the 'between-groups' synchronization process (e.g., serially renumber sensor location(s) in image(s)) for a reason that is described herein. The sensor locations detected in each image may be initially serially numbered or labelled 1, 2, 3, . . . , j in the image regardless of their location in a catheter/sensing element. (T represents the number of sensor locations detected in each image, and j may change between images.) Therefore, a sensor location numbered m (1≤m≤j; e.g., m=1) in one image, and a sensor location having the same number in another image do not necessarily refer to or represent the same sensor in the sensing element. Sensor locations may be labelled in a way other than numbering; e.g., sequential labels (e.g., A, B, C, . . . or another format) may be used as "numbering" or labelling. It may occur, for example, that a sensor location numbered, say, four (4) in one image and a sensor location having a different number (e.g., seven) in another image refer to, or represent, the same sensor in the sensing element. Referencing a same sensor by different numbers in different images may make it difficult, for example to a viewer or to a controller or processor, to 'understand' where a particular sensor of the sensing element appears in the images. In addition, referencing a same sensor by different numbers in different images may make the detection of additional sensors, or sensor locations, more challenging. This problem may be mitigated by the processor performing a 'between-groups' synchronization/adjustment process, whereby the processor assigns the same number to every sensor location (one sensor location in an image) that refers to or represents a same particular sensor in the sensing element.

After the between-groups synchronization process is completed or terminated, the controller or processor may pervade or propagate the 'two-direction' iterative process described herein to find (e.g., estimate) candidate sensor locations, and to estimate locations of sensors in bad images whose location has not yet been identified or determined.

At step 228, the controller or processor may improve/enhance sensor detection in the entire series of images (e.g., image series 210) in term of sensor locations by using, for example, spatial and/or temporal, or spatiotemporal, interpolation. For example, improving/enhancing the sensor detection may be done by using spline interpolation or model-based-constrained interpolation. Step 228 is more fully described in connection with FIG. 4, which is described below.

'Spatial interpolation' is an interpolation process in/by which an expected location of a 'missing' sensor (an indiscernible sensor) in an image is determined by using locations of other sensors within the same image; that is, using sensor locations captured or imaged at a same time. 'Temporal interpolation' is an interpolation process in/by which an expected location of a 'missing' sensor (an indiscernible sensor) in a particular image is determined by using sensor locations of sensors in other images; that is, using locations of sensors that were imaged at different times (e.g., one image that chronologically precedes the particular image and one image that chronologically follows the particular image, hence usage of the term "temporal").

Figure 3A:
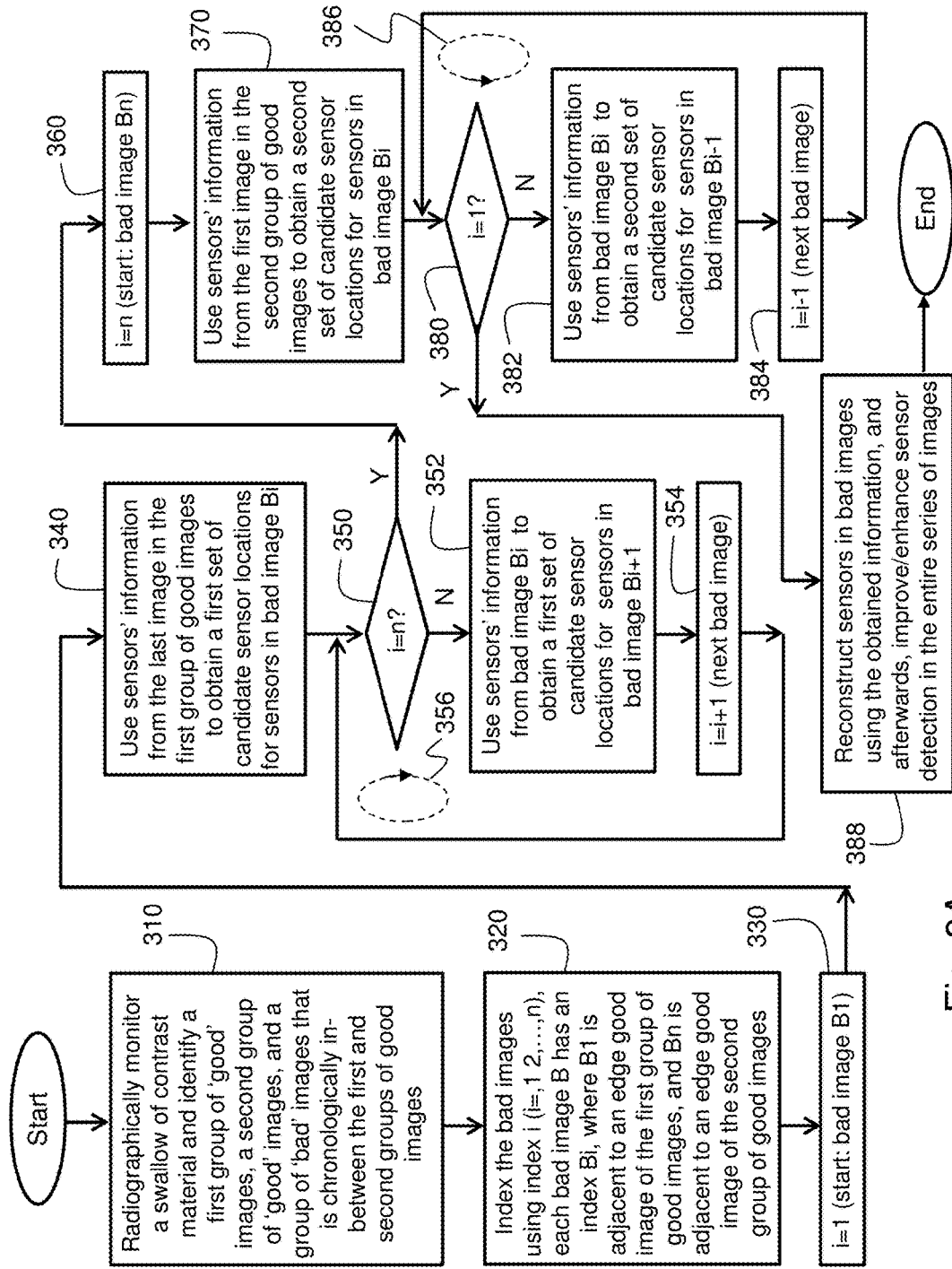
FIG. 3A shows a method for reconstructing sensor locations for radiopaque sensors in radiographic image(s) according to another example embodiment.

FIG. 3A shows a method for estimating sensor locations in bad images according to another example embodiment of the present invention. At step 310, a controller or processor may monitor a swallow of contrast material and identify two groups (e.g., first and second groups) of good images and a (third) group of bad images, with the first group of good images; e.g., group 250 of FIG. 2B, chronologically followed by the (third) group of bad images; e.g., group 260 of FIG. 2B, which, in turn, is chronologically followed by the second group of good images; e.g., group 270 of FIG. 2B. Step 310 may be identical or similar to step 'block' 232 of FIG. 2C, for example step 310 may include one step or more than one step of steps 212-218, 222 and 224 of FIG. 2C.

At step 320, orderly (chronologically) index/number the bad images (e.g., group 260) using index i (i=1, 2, ..., n), where B1 chronologically precedes bad image B2, bad image B2 chronologically precedes bad image B3, and so on, and where image B1 is chronologically subsequent, adjacent or contiguous to the chronologically last good image of the first group of good images (e.g., bad image B1 is chronologically subsequent to good image 280 of group 250, FIG. 2B), and where Bn is the chronologically last bad image in the group of good images and chronologically precedes, adjacent or contiguous to the chronologically first good image of the second group of good images (e.g., bad image Bn precedes good image 290 of group 270, FIG. 2B).

At step 330, set an initial value to index i (e.g., i=1). At step 340, use sensors' information from, or related to sensor locations in, an image (e.g., the last chronological image) in the first group of good images (e.g., last image 280 in group 250, FIG. 2B) to obtain a first set of candidate sensor locations, $S_{CLi}^1$, for sensors in bad image Bi, and to enable, improve or enhance, detection or estimation of sensor locations for sensors in bad image Bi (e.g., in bad image B1). If some sensor location information is available for image B1 prior to step 340, it can be used at, by or during step 340. The process performed at step 340 may create, or it may enable to obtain, the first set of candidate sensor locations, $S_{CLi}^1$, for sensors in bad image Bi (e.g., B1). Sensor information may include information referring to or representing locations of all or some of the sensors in the last good image. (A sensor location that is estimated by using the iterative process described herein is referred to herein as a 'candidate sensor location'.) In addition, the last good image in the first group of good images may be useful in estimating sensor locations (e.g., estimating candidate sensor locations) in a chronologically subsequent or adjacent bad image because the sensors are not expected to move much from a time when one image is captured to a time when a subsequent image is captured. (The higher the images capturing rate, the lesser the expected movement.)

At step 350, check whether the value i is equal to n, where the number n is the number of bad images in the group of bad images (e.g., group 260). If i has a value which is less than n (the condition is shown as "N" at step 350), then, at step 352, use sensor information from/in, or related to sensor locations in, bad image Bi (e.g., image B1, if 1=1) to determine or estimate a first set of candidate sensor locations, $S_{CLi}^1$, for sensors in the chronologically subsequent bad image $B_{i+1}$ (e.g., for bad image B2).

Sensor locations in bad image $B_i$ (e.g., image B1) may include an estimated first set of candidate sensor locations and, depending on the discernibility of sensors in image Bi, also discernible sensor locations. (A 'discernible' sensor location is a location of a sensor that is detectable in a radiographic image on its own merit, therefore it does not have to be estimated from or using another sensor location in the same image or in another image.). If some sensor location information is available for Bi+1 prior to step 352, it can be used at step 352.

At step 354, increment index i by one (i.e., i=i+1) to initiate estimation of a first set of candidate sensor locations for the next bad image $B_{i+1}$ (e.g., bad image B3, to continue the example). Then, using loop 356, repeat or iterate steps 352 and 354, as long as i<n, in order to iteratively or repeatedly cascade, propagate, or pervade the first set of candidate sensor locations, $S_{CLi}^1$, from one bad image (e.g., i=1) to another (e.g., i=2), in a first (forward) temporal direction. For example, repeating step 352, sensor location information estimated for bad image $B_{i+1}$ (e.g., set $S_{CL3}^1$ corresponding to image B3) may be used to estimate a first set of candidate sensor locations for sensors in bad image $B_{i+2}$ (e.g., set $S_{CL4}^1$ corresponding to bad image B4), and so on. ('Sensor information', per radiographic image, may include information regarding locations of sensors that are estimated using the preceding bad image, e.g., the first set of candidate sensor location. 'Sensor information' may also include information regarding locations of sensors which are discernible/visible in the pertinent radiographic image.)

If the value of i is n (this condition is shown as "Y" at step 350), iteration loop 356 may be terminated. A processor implementing the method of FIG. 3A may determine a first set of candidate sensor locations in image B1 from sensor locations in an image of the first group (e.g., group 250, FIG. 2B) of images, and, by starting from i=1, determine iteratively (e.g., using iteration loop 356) a first set of candidate sensor locations in image Bi+1, until a first set of candidate sensor locations is determined in image Bn. Iteration of loop 356 may result in a group of first sets of candidate sensor locations, $\{S_{CL1}^1, S_{CL2}^1, \ldots, S_{CLn}^1\}$, where $S_{CL1}^1$ is a first set of candidate sensor locations found, calculated or estimated for bad image B1, $S_{CL2}^1$ is a first set of candidate sensor locations found, calculated or estimated for bad image B2, and so on. (The first set of candidate sensor locations estimated for a particular bad image Bi may respectively include one candidate sensor location for each sensor in that image, or none.)

As the sensor locations estimation process pervades 'forward' from one bad image (Bi) to another ($B_{i+1}$), accuracy of the resulting candidate sensor locations may lessen from one image to another. To mitigate this deficiency, a similar sensor location estimation process may likewise be applied to the group of bad images in the reversed (backward) order in order to obtain a second group of sets of candidate sensor locations, $\{S_{CL1}^2, S_{CL2}^2, \ldots, S_{CLn}^2\}$, where $S_{CL1}^2$ is a second set of candidate sensor locations found, calculated or estimated for bad image B1, $S_{CL2}^2$ is a second set of candidate sensor locations found, calculated or estimated for bad image B2, and so on. Then, a location for a particular sensor, $S_k$, in a particular bad image, Bi, may be determined using two candidate sensor locations $\{S_{CL\_k\_i}^1, S_{CL\_k\_i}^2\}$: one candidate sensor location ($S_{CL\_k\_i}^1$) that was estimated for this particular sensor during the first (forward) sensor location estimation iterative process, and another candidate sensor location ($S_{CL\_k\_i}^2$) that was estimated for the particular sensor during the second (backward) sensor location estimation iterative process. (This principle, for determining a location of sensor in a bad image, may similarly be applied to other sensors in the particular bad image as well as to sensors in other bad images.)

In order to determine whether two (a pair of) candidate censor locations $\{S_{CL\_k\_i}^1, S_{CL\_k\_i}^2\}$ for a particular sensor ($S_k$) in a particular bad image (Bi) can be used to, for example, estimate a location for/of the sensor in this bad image, the two candidate sensor locations (e.g., $S_{CL\_k\_i}^1$ and $S_{CL\_k\_i}^2$) may be checked for spatial/positional consistency or similarity on individual basis. That is, consistency, similarity or congruency between two candidate sensor locations may be checked for a sensor in a bad image irrespective of other sensors in the same image or in other images.

Corroborating a first set of candidate sensor locations may be initiated by repeating the candidate sensor locations estimation process in the reversed order, as described herein to obtain another set of candidate sensor locations, and comparing the resulting two sets of candidate sensor locations. The corroboration process may start, for example, at step 360, in which the value of i may initially be set to n (to propagate the sensor locations in the reversed order, or 'backwards', for example from the chronological first good image 290 following the group of bad images to Bn, from Bn to Bn−1, and so on, until B1).

At step 370, use sensor information from/in, or related to sensor locations in a good image (e.g., in the chronologically first good image) in the second group of good images (e.g., good image 290 in image group 270, FIG. 2B) to obtain a second set of candidate sensor locations, $S_{CLi}^2$, for sensors in bad image Bi (i.e. Bn), and to enable, improve or enhance, detection or estimation of locations for sensors in bad image Bi. This process may create, or it may enable to obtain, the second set of candidate sensor locations for sensors in bad image Bi (e.g., Bn). If some sensor location information is available for Bi (i.e. for $B_n$) prior to step 370, it can be used at step 370.

At step 380, check whether i is equal to one. If i has a value which is greater than one (the condition is shown as "N" at step 380), then, at step 382, use sensor information from/in bad image Bi (e.g., image Bn) to estimate the second set of candidate sensor locations in a chronologically preceding bad image $B_{i-1}$ (e.g., $B_{n-1}$). At step 384 decrement index i by one (i.e., i=i−1) to initiate determination or estimation of the second set of candidate sensor locations for the next bad image to be processed (that is, for a further preceding bad image). If some sensor location information is available for Bi−1 prior to step 382, it can be used at step 382.

Loop 386 may be repeated or iterated as long as i>1, in order to iteratively or repeatedly cascade, propagate or pervade the sensor information from one bad image to another, in the opposite direction (relative to the propagation direction during iterative loop 356). For example, repeating step 382, sensor information of bad image Bi−1 (that is, the second set of candidate sensor locations obtained for bad image $B_{i-1}$ and locations of sensors which are clearly discernible/visible in the pertinent radiographic image) may be used to estimate the second set of candidate sensor locations for sensors in bad image $B_{i-2}$, and so on.

If i has a value that is equal to 1 (this condition is shown as "Y" at step 380), loop 386 may be terminated. The processor implementing the method of FIG. 3A may also determine a second set of candidate sensor locations in image Bn from sensor locations in an image of the second group (e.g., group 270, FIG. 2B) of images, and, by starting from i=n, determine iteratively (e.g., using iteration loop 386) a second set of candidate sensor locations in image Bi−1, until a second set of candidate sensor locations is determined in image B1. Iteration of loop 386 may result in a group of second sets of candidate sensor locations, $\{S_{CL1}^2, S_{CL2}^2, \ldots, S_{CLn}^2\}$, which includes a set of candidate sensor locations, $S_{CLi}^2$, for each bad image Bi. For example, $S_{CL1}^2$ is a second set of candidate sensor locations found, calculated or estimated for bad image B1, $S_{CL2}^2$ is a second set of candidate sensor locations found, calculated or estimated for bad image B2, and so on. (The second set of candidate sensor locations estimated for a particular bad image Bi may respectively include one candidate sensor location for each sensor in that image, or none.) At this stage, two sets of candidate sensor locations may be associated with (estimated for) each bad image Bi, and a sensor in a bad image may have associated with it a pair of candidate sensor locations that were estimated for it: one candidate sensor location in each set of candidate sensor locations. The pair of candidate sensor locations may be used to determine the location of the sensor in the particular bad image.

At step 388, pertinent pairs of candidate sensor locations that were obtained or determined by using loops 356 and 386 may be used to estimate sensor locations in bad images. That is, sensor locations in each image Bi of images B1, . . . , Bn may be estimated using the pertinent first and second sets of candidate sensor locations; i.e., the first set of candidate sensor locations obtained during, or as a result of, the iteration loop 356, and the second set of candidate sensor locations obtained during, or as a result of, the iteration loop 386. (The sensor locations estimation process is described further in connection with, for example, FIG. 3B, which is described below.) After sensor locations are estimated, the sensor locations determination or estimation process may be improved or enhanced in order to estimate other sensor locations for the entire series of images; e.g., the image series comprising the first and second groups (the groups of good images), and the third group (the group of bad images). (The improvement/enhancement process is described in more detail in connection with, for example, FIG. 4, which is described below.)

A decision, as to whether a particular sensor location in a particular bad image, Bi, may be estimated, may depend on the pertinent pair of candidate sensor locations; that is, on the two candidate sensor locations that were estimated for the particular sensor in the particular bad image by using the two iterative processes. For example, a location of a particular sensor may be estimated if the related pair of candidate sensor locations obtained or resulted from the two iterative processes are consistent, or congruent, within a predetermined margin, that is, if they are similar, coincident, close 'enough', in agreement or overlap at least to some degree; e.g., at least 50% overlap exists between the two locations. The consistency, or congruency, degree or threshold and/or the consistency, or congruency, margin may be selected according to a parameter. The parameter may be related to, refer to, derived from or include, for example, the appearance of the imaged body organ (e.g., clarity or obscurity of the imaged organ), the number (m) of sensors in the sensing element (e.g., the greater the number of sensors, the smaller/stringent the consistency/congruency margin, and vice versa), the density of the sensors in the sensing element, the quality of the radiographic images in general, the type of the imaging system, the type of the used contrast material, etc.

Figure 3B:
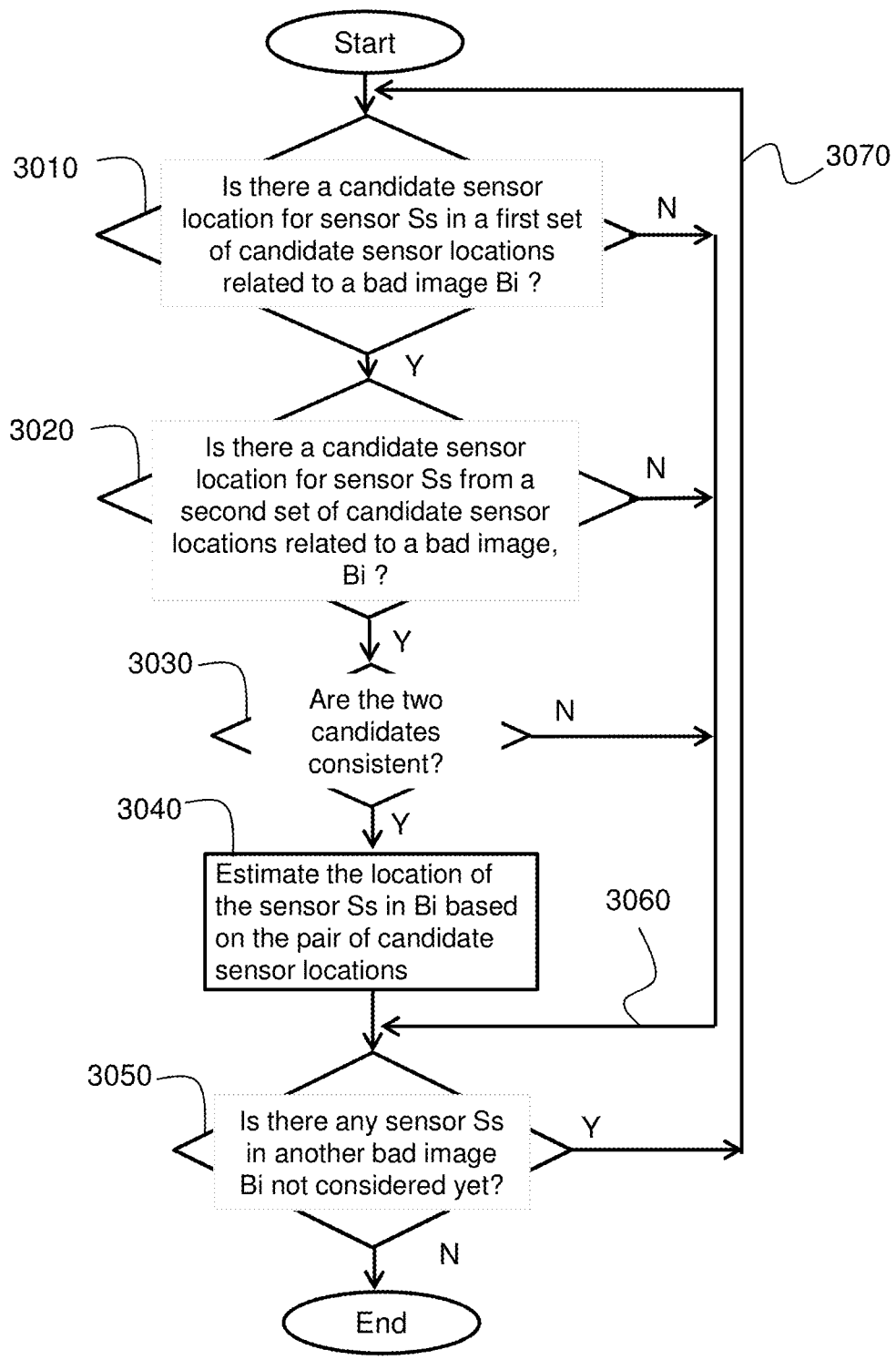
FIG. 3B shows a method for estimating or enabling determination of sensor locations in a radiographic bad image based on two sets of candidate sensor locations according to an example embodiment.

FIG. 3B shows a method for estimating or enabling determination of sensor locations in a radiographic bad image based on two sets of candidate sensor locations according to an example embodiment. (Assume that the sensor locations determination process described, for example, in connection with FIG. 3B is applied to a particular bad image, Bi, selected from a group of bad images (e.g., group 260, FIG. 2B), for example to a first chronologically captured image (e.g., image B1) in the group of bad images. A similar process may, though, be applied to other bad images.)

For each particular sensor Ss in each particular bad image Bi a controller, or a processor, may perform the steps described below. At step 3010, the controller, or processor, may check whether there is a candidate sensor location for sensor Ss in a first set of candidate sensor locations related to (e.g., estimated for) the particular bad image Bi in the particular bad image Bi.

If there is no candidate sensor location for sensor Ss in the first set of candidate sensor locations estimated for, or in relation with, the particular bad image Bi (the condition is shown as "N" at step 3010), this means that the location for the currently selected sensor in the currently selected bad image Bi cannot be determined by using a pair of candidate sensor locations. Therefore, the controller/processor may be redirected (3060) to step 3050. However, if there is a candidate sensor location for sensor Ss in the first set of candidate sensor locations estimated for, or in relation with, the particular bad image Bi (the condition is shown as "Y" at step 3010), then the controller/processor may check, at step 3020, whether there is a candidate sensor location for sensor Ss also in a second set of candidate sensor locations related to (estimated for) the same particular bad image Bi.

If there is no candidate sensor location for sensor Ss in the second set of candidate sensor locations (the condition is shown as "N" at step 3020), this means that the location for the currently selected sensor (sensor Ss) in the current bad image cannot be determined by using a pair of candidate sensor locations. Therefore, the controller/processor may be redirected (3060) to step 3050. However, if there is a candidate sensor location for sensor Ss also in the second set of candidate sensor locations estimated for, or in relation with, the particular bad image Bi (the condition is shown as "Y" at step 3020), then the controller/processor may check, at step 3030, whether the two candidate sensor locations related to sensor Ss in the current bad image are consistent/congruent (within a margin).

Candidate sensor locations may be consistent/congruent if they are identical, similar, in agreement or overlapping in terms of, for example, a coordinate system (for example they may have similar {X;Y} coordinates in an image) which is applied or used to define locations of (e.g., graphical) objects in radiographic images. Alternatively, a number of pixels separating or interposed between two candidate sensor locations may be used to determine consistency/congruency (e.g., calculate consistency or congruency grade, score or rank) between the two candidate sensor locations. For example, the lower the number of pixels interposed between two candidate sensor locations, the shorter the distance (the narrower the gap) between the candidate sensor locations and, therefore, the greater the consistency between these locations; that is, the more congruent these locations are.

If the two candidate sensor locations are inconsistent or incongruent, or a consistency or congruency grade, score or rank indicating a consistency or congruency degree between the two candidate sensor locations is below a threshold value (the condition is shown as "N" at step 3030), this means that the location of currently selected sensor Ss in the currently selected bad image cannot be determined (e.g., calculated) by using the two candidate sensor locations estimated for it, because the two candidate sensor locations are too far from each other. Therefore, the controller/processor may be redirected (3060) to step 3050. However, if the two candidate sensor locations are consistent/congruent (the condition is shown as "Y" at step 3030), then, at step 3040, the controller/processor may estimate the location of sensor Ss in bad image Bi based on (e.g., driving its location in image Bi from) the pair of candidate sensor locations.

At step 3050, the controller/processor may check whether there is at least one more sensor Ss whose location is to be estimated in any bad image Bi. If there is at least one more such sensor (the condition is shown as "Y" at step 3050), steps 3010-3050 may be repeated for this additional sensor. However, if there are no more such sensors (the condition is shown as "N" at step 3050), the sensor locations estimation process may be terminated.

While execution of steps 3010-3040, or loop 3070, one time enables, for example, a controller or processor, to determine a location of one sensor (e.g., sensor Ss) in a bad image Bi, the controller/processor may repeat these steps, or loop 3070, to estimate locations of additional sensors in the same bad image as well as in other bad images. It may be that all sensor locations in a bad image Bi may be estimated by respectively using pertinent pairs of consistent candidate sensor locations, or only some of the sensor locations in a/the bad image may be estimated this way. If not all of the sensor locations in a particular bad image can be estimated by using the process described above, then the sensor locations in that particular bad image which are not (e.g., cannot be) estimated from, or by using, candidate sensor locations may be interpolated using, based on, or from sensor locations in image(s) that were already estimated. (The process of estimating additional sensor locations is described in more detail in connection with FIG. 4.)

Figure 4:
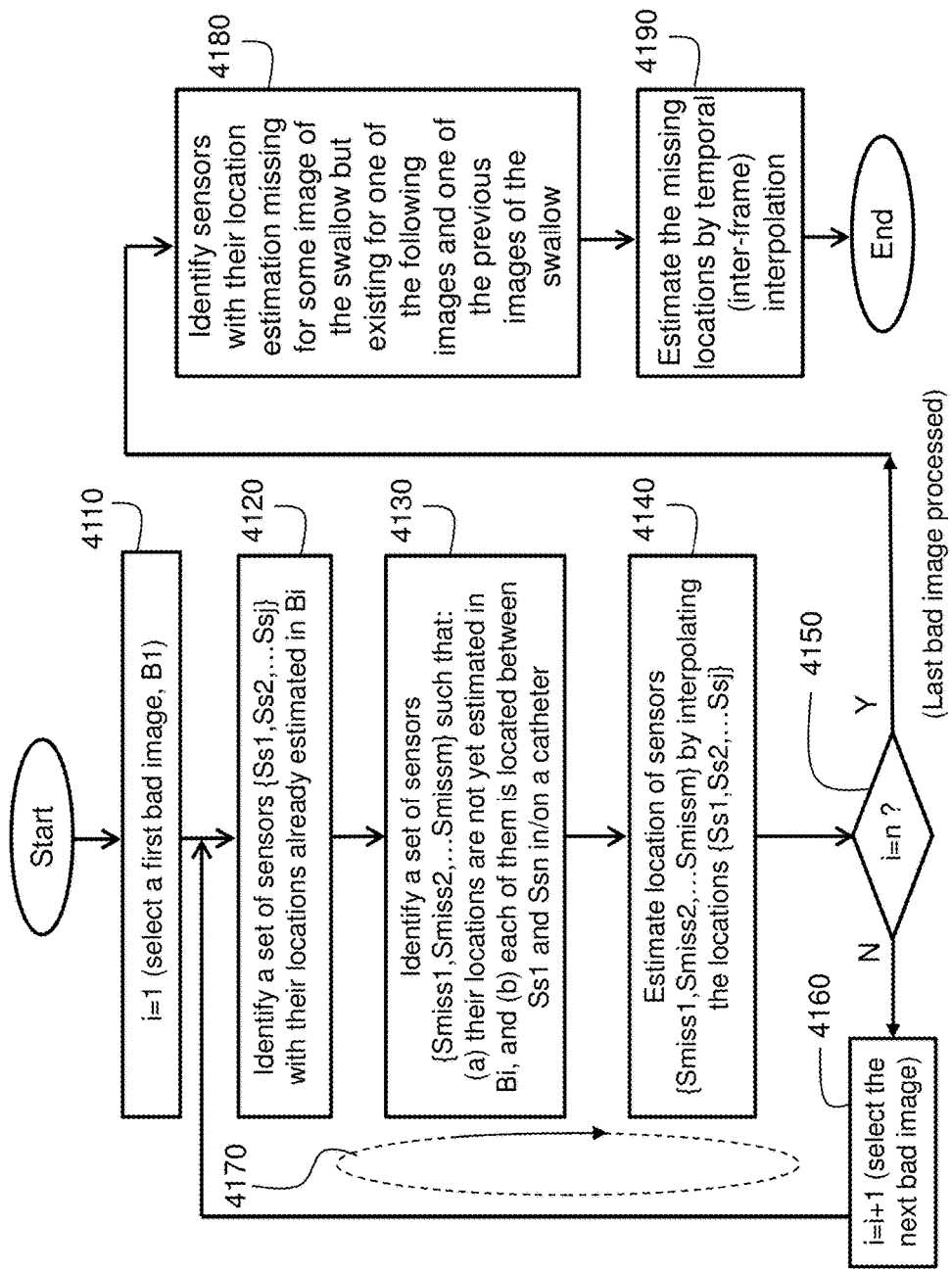
FIG. 4 shows a method for reconstructing additional sensor locations in images according to an example embodiment.

FIG. 4 shows a method for obtaining sensor information for estimating additional sensor locations in images according to another example embodiment. At step 4110, set the value of index i to one to select a first bad image, B1, which may be a chronologically first captured bad image in the group of bad images B1, B2, . . . , Bn. At step 4120, identify a set of sensors {Ss1, Ss2, . . . Ssj} with their locations already estimated in Bi by using the two-way, or bidirectional, sensor locations estimation iterative process described herein, for example, in connection with FIG. 3A. At step 4130, identify a set of sensors {$Smiss_1$, $Smiss_2$, . . . , $Smiss_1$} whose locations are not estimated yet in Bi, for example because they could not be estimated in the bad image by using the two-directional sensor locations estimation iterative process. Identify this set of sensors such that each of these sensors is located between the first sensor Ss1 with estimated location and the last sensor Ssj with estimated location in a sensing element (e.g., catheter). 'l' (in $Smiss_l$) is less then m ('m' is the number of sensors in the imaged catheter). At step 4140, estimate the location of each of sensors {$Smiss_1$, $Smiss_2$, . . . , $Smiss_l$} in image Bi by interpolating locations of sensors {Ss1, Ss2, . . . , Ssj} already estimated for image Bi, for example by using spline interpolation or model-based-constrained interpolation.

At step 4150 it is checked whether there are additional bad images for which sensor locations need to be interpolated. If there is another bad image for which sensor locations need to be interpolated (this condition is shown as "N" at step 4150), increase the value of index i by one (i=i+1) in order to reiterate or repeat loop 4170 for the next bad image Bi+1. However, if i=n (this condition is shown as "Y" at step 4150), the iteration loop may be terminated. Terminating of iteration loop 4170 may mean that sensor locations have been interpolated for each bad image in the group of bad images B1, . . . , Bn. At each iteration, the iterative process (loop 4170) may use only intra image sensor information to estimate additional sensor locations in a particular bad image Bi, and, in doing so, the iterative process (4170) does not use sensor information related to any other good image or bad image.

After additional sensor locations are estimated for/in bad images via intra image interpolation, steps 4180 and 4190 are performed across, on, or they are applied to, the entire series of chronologically captured radiographic images (e.g., series 210 of images; cf. FIGS. 2A-2B). At step 4180, identify, across the series of swallow images (e.g., images 210), a sensor whose location is 'missing' in (e.g., was not estimated for) a particular image in the series of the swallow images but estimated for a chronologically preceding image and for a chronologically subsequent image. At step 4190, estimate the location of the identified sensor that is missing in the particular image by performing temporal (inter frame/image) interpolation, that is, by using, in the interpolation, the sensor locations estimated for the same sensor in the other (preceding and subsequent) images.

Steps 4110-4190 may enable, for example a controller or processor, to determine or estimate sensor locations in bad images by using 'spatial' interpolation within each image (e.g., using intra image interpolation), and to determine or estimate sensor locations in images (bad or good) by using 'temporal' interpolation (e.g., inter image interpolation).

Figure 5A:
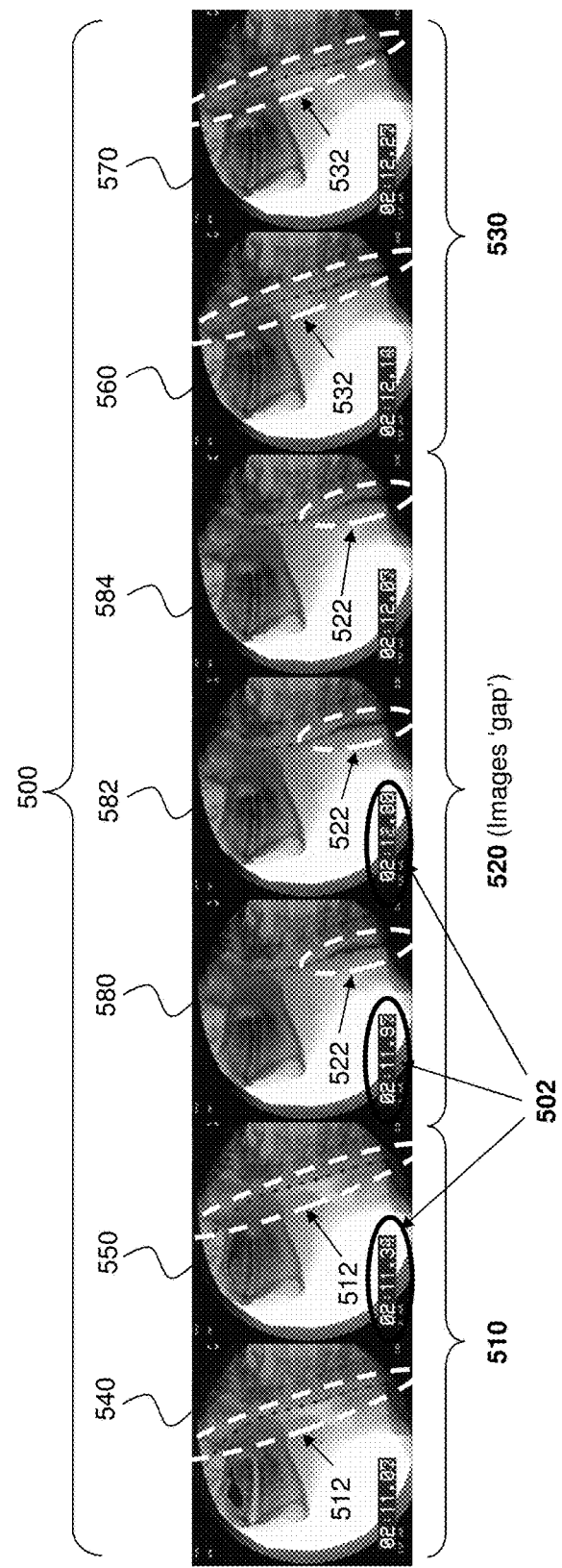
FIGS. 5A-5H depict example radiographic images overlaid with the results of different stages of sensor location estimation process applied to a sequence/series of radiographic images of a single swallow, according to embodiments of the invention.
Figure 5B:
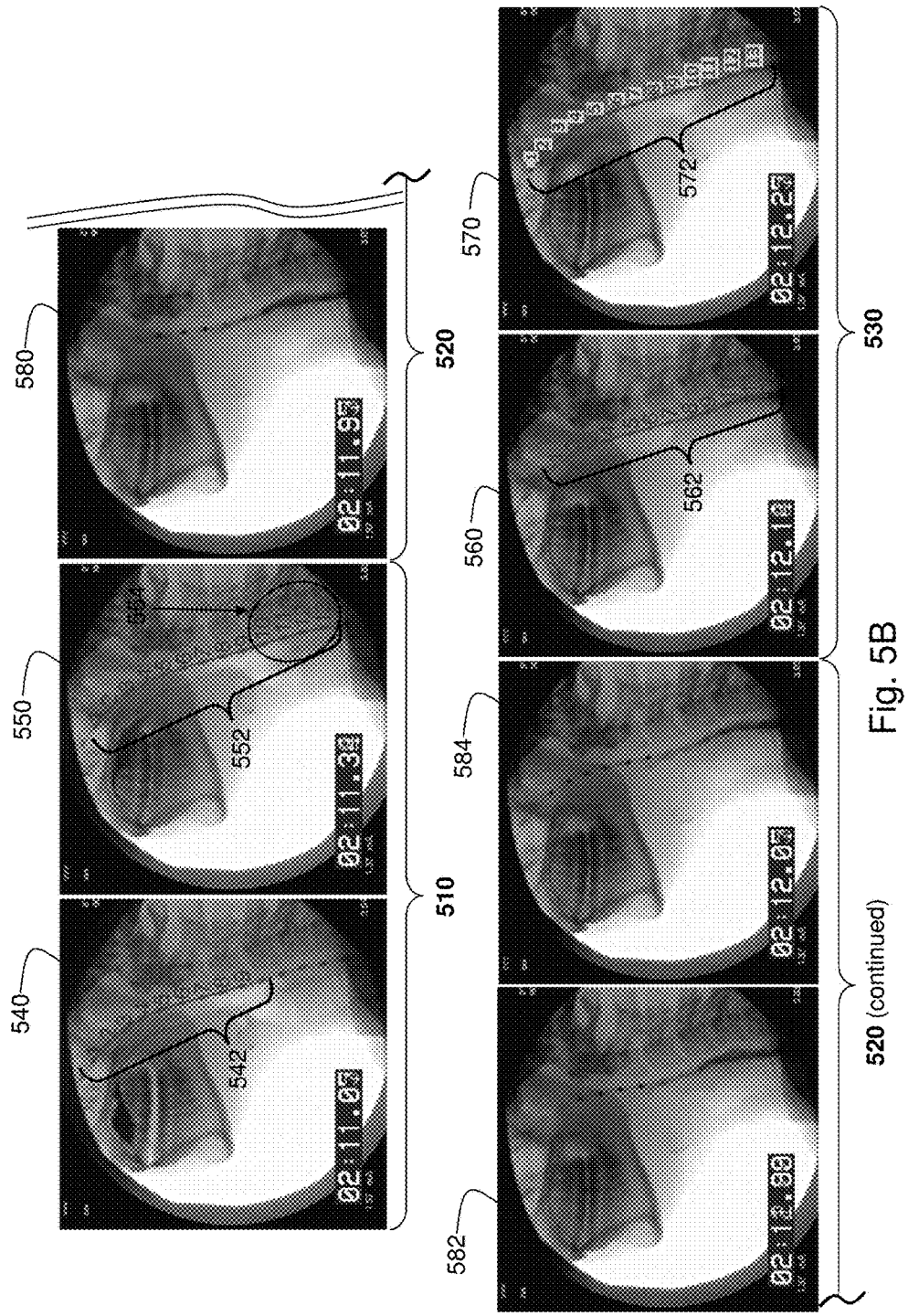
Figure 5C:
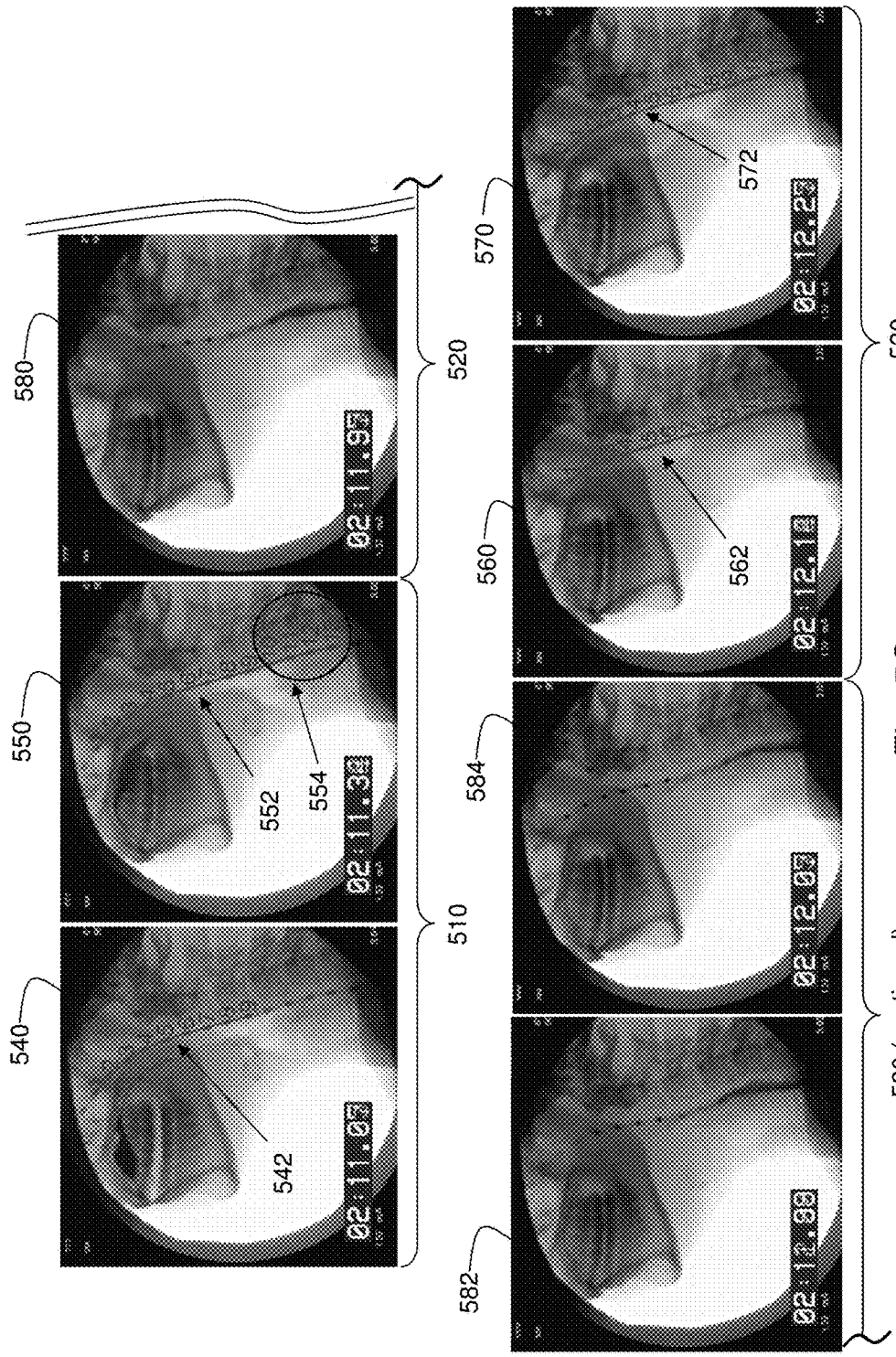
Figure 5D:
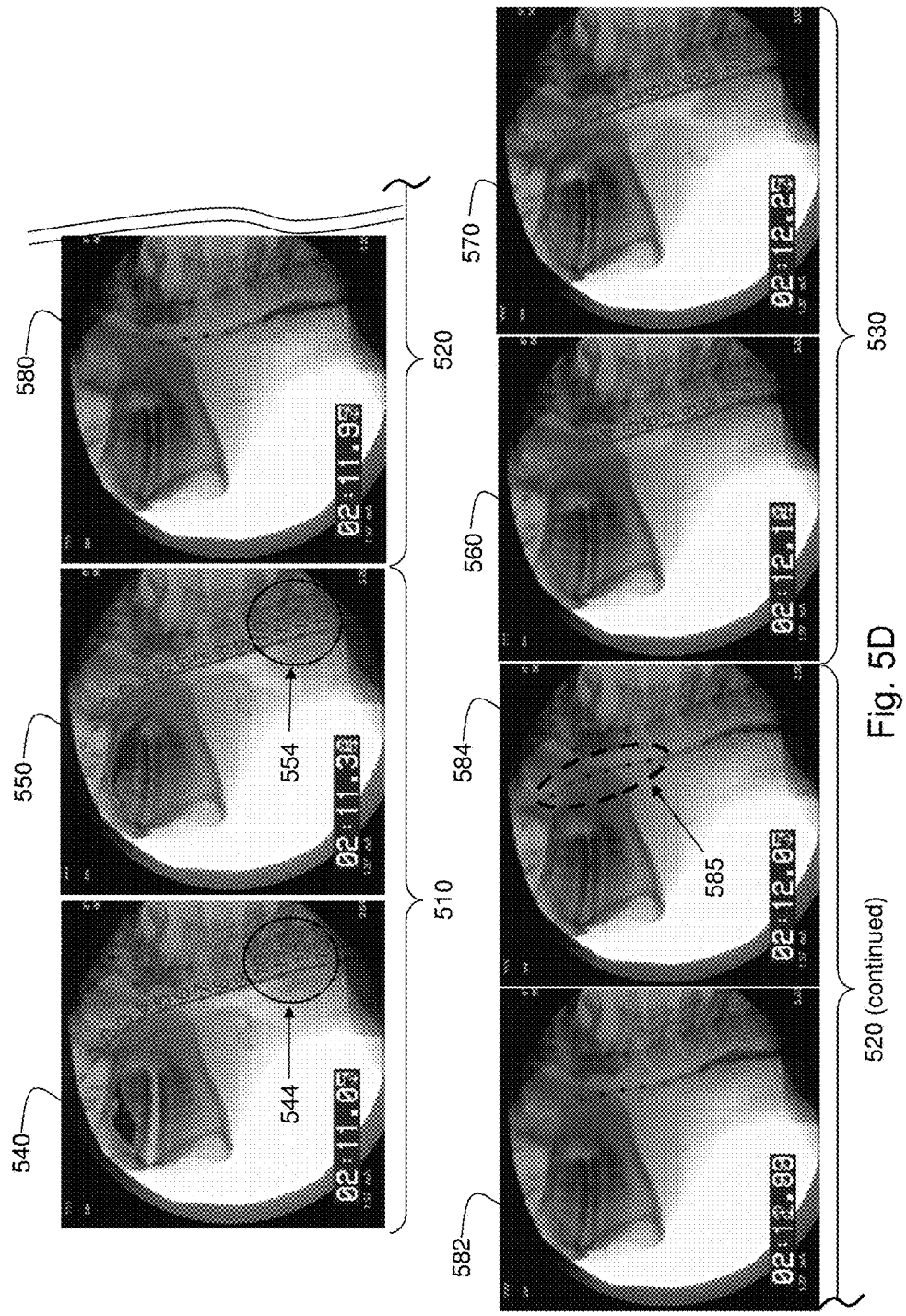

FIGS. 5A-5G depict example results of an entire sensor location estimation process of a sequence/series of radiographic images of a single swallow (e.g., single swallow 210, FIGS. 2A-2B). FIG. 5A depicts a single chronologically acquired swallow sequence 500 of radiographic images according to an example embodiment of the present invention. Reference numeral 502 denotes example capturing times, or timestamps, of example radiographic images. For example, the timestamp of example image 580 is "02:11.97". (Images' timestamps may be used to chronologically order images within each group of images and image groups.) Swallow images sequence 500 may include a first group 510 of good images that includes chronologically ordered radiographic images in which most or many of the sensors of a sensing element (e.g., sensing element 112, FIG. 1A) are radiographically discernible, as shown at 512; an image group/'gap' 520, which includes chronologically ordered sequence of bad images, where a 'bad' image is an image in which all, most or many of the sensors are radiographically indiscernible, as shown at 522, and a second group 530 of good images that includes chronologically ordered radiographic images in which most or many of the sensors are radiographically discernible, as shown at 532. Many/most of the sensors in the two groups of good images are clearly discernible (visible) and, as such, they can be detected by a processor (as distinct little dots) in contrast material free images 540, 550, 560 and 570. In images 580, 582 and 584 many sensors are indiscernible, or occluded or opacified, by the contrast material. A group of bad images (e.g., group 520) may be selected such that the group is chronologically interposed or placed between a first group of good images (e.g., group 510) and a second group of good images (e.g., group 530). Discernible sensors (sensor locations) are first estimated and serially indexed 1, 2, 3, . . . , g in each image separately; that is, independently of how many or which sensors are discernible in the other images, as pictorially shown in 5B.

FIG. 5B depicts sensors that are serially indexed/numbered within each good image separately and independently, that is, regardless of or without consideration of other images or sensors or sensor locations in other images. That is, reconstructed discernible sensor locations within each image within each of the first group (510) and second group (530) of images are initially numbered regardless of other images. For example, the locations of nine and thirteen discernible sensors are respectively identified/detected in good images 540 and 550 of the first group 510 of good images, and initially ordered numerically as respectively shown at 542 and 552. For example, the nine sensor locations shown at 542 are initially serially numbered 1, 2, . . . , 9, and the thirteen sensors shown at 552 are initially serially numbered 1, 2, . . . , 13. Likewise, the location of twelve and thirteen sensors are respectively identified/detected in good images 560 and 570 of the second group 530 of good images and initially ordered numerically as respectively shown at 562 (sensor locations 1, 2, . . . , 12 in image 560) and at 572 (sensor locations 1, 2, . . . , 13 in image 570). Sensors that are detected/identified in a particular good image (e.g., good image 550) are serially/orderly numbered regardless of their locations in the image, and regardless of how many sensors are detected/identified in other good images (e.g., in good images 540, 560, 570), or where sensors are located in the other good images. (In bad images 580, 582 and 584 of group 520 of bad images a few sensors may be detectable but they are not numbered at this stage.)

As demonstrated in FIG. 5B, there is a spatial shift in the sensor initial numbers between images 560 and 570. That is, a same sensor location has been assigned different numbers in the two images. (As described above, in the stage, or method step, demonstrated in FIG. 5B sensors are numbered serially, and not according to their locations in the image.) For example, the sensor (or sensor location) numbered four (4) refers to different sensors in images 560 and 570. (Continuing the example, sensor location number four refers to a higher sensor in image 570 than in image 560.) The problem described above, of a sensor that is assigned different numbers, is mitigated as demonstrated in FIG. 5C.

In FIG. 5C, each group of good images undergoes an internal (intra) synchronization process (e.g., serially renumbering of sensor locations) in order to assign the same index number to locations of a sensor in different images of a same group, where the sensor locations in the different images of the same group are related or correspond to, or represent the same sensor. The intra synchronization process may include synchronizing sensor numbers internally in each of the first group (510) and second group (530) of images, the synchronization may include serially, and independently for each group, renumbering reconstructed discernible sensor locations within each of the first and second image groups such that a same serial number within all images of the first group refers to the same imaged sensor, and a same serial number within all images of the second group refers to the same imaged sensor.

Synchronizing between sensor numbers within each group of good images may be performed, for example at this stage, regardless, or without consideration, of good images in the other group. The internal synchronization process may be performed based on, for example, (a) visual similarity of the same sensor in the adjacent images, and (b) the fact that a sensor's location does not change significantly (pixelwise) between temporally adjacent or subsequent frames. Synchronization between sensors' numbers may be performed by, for example, using a radiographically discernible/detectable (e.g., radiopaque) reference member (e.g., fiducial indicia) that may be mounted on or in, or otherwise be incorporated into, for example, the imaged sensing element. FIG. 5C depicts sensors' numbers assigned to sensors after the numbers synchronization within each group of good images is performed. After synchronization is performed, the same numbers are respectively assigned to, or represent or correspond to, the same sensors in frames 560 and 570, as is demonstrated in FIG. 5C. For example, after the synchronization process is performed, the sensor (or sensor location) numbered, for example, one (1) refers to the same sensor in images 560 and 570.

FIG. 5D depicts enhancement of sensor locations within each of the first group (510) and second group (530) of images. (Sensor locations a good image in a particular group may be determined using other images in the same group.). The enhancement may include, for each particular image group, estimating location of additional sensors in any image of the particular group based on sensor locations of discernable sensors already reconstructed in other images of the same particular group. For example, sensor locations 10-13, shown at 554, which were identified/detected in good image 550 (but not in good image 540. See image 540 in FIG. 5C), are or may be used to estimate or enhance sensor locations in adjacent good image 540, for example, by adding sensor locations 10-13 to good image 540 at the suitable locations. The sensor locations added in FIG. 5D in good image 540 are shown at 544.

Figure 5E:
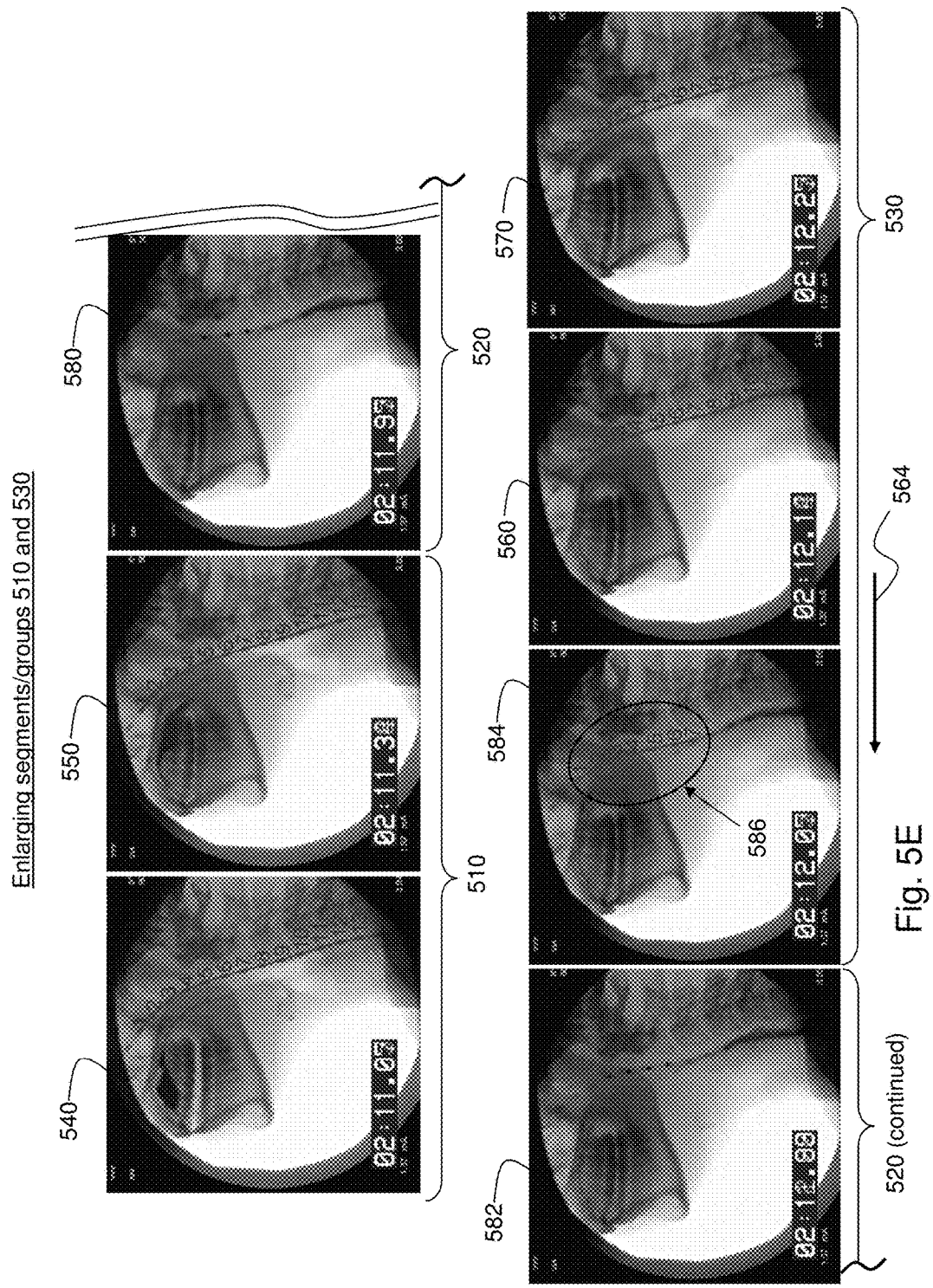

FIG. 5E depicts enlargement of group 530 of good images (and possible partial or full 'closure' of images 'gap' 520). Enlarging the first group (510) and the second group (530) of images may likewise be generally performed by improving sensor estimation results in the images of third group (520) of images adjacent to either the first or the second groups of images.

Referring to FIG. 5E, sensor locations in good image 560 may be used to improve detection of sensor locations 586 (in this example sensor locations 1-7) in bad image 584 that is chronologically adjacent/contiguous to group 530 of good images. By way of example, the number of sensor locations detected in image 584 is increased from six (as shown at 585 in FIG. 5D) to seven (as shown at 586 in FIG. 5E). If the improvement provides for the detection of enough sensor locations (e.g., per a predetermined image classification threshold), then bad image 584 may become (may be classified as) a 'good' image and, therefore, it can be removed or deleted from group 520 of bad images and, instead, it can be added to or joined with (to extend) group 530 of good images. Good image 560, which is an example of chronologically captured first good image of images group 530, may be used as a first good image to (attempt to) pervade a sensor locations estimation process, or to pervade estimated candidate sensor locations, 'through' group 520 of bad images, in a right-to-left direction (in direction 564), for example from bad image 560 to bad image 584, from bad image 584 to bad image 582, and so on, to, thereby, enlarge/extend group 530 of good images, in this example to the left hand side direction (564).

A controller may repeat the iterative process described above to narrow down the image gap (e.g., reducing the group of bad images) in the stream of images as much as possible, preferably until the two groups of good images 'meet' (by extending them towards one another), in which case the images gap would be zeroed. However, in some cases, the sensor information obtained during the gap closing process may not suffice to zero the images gap, in which case some bad images may still remain in the image stream after the process is completed/terminated.

Figure 5F:
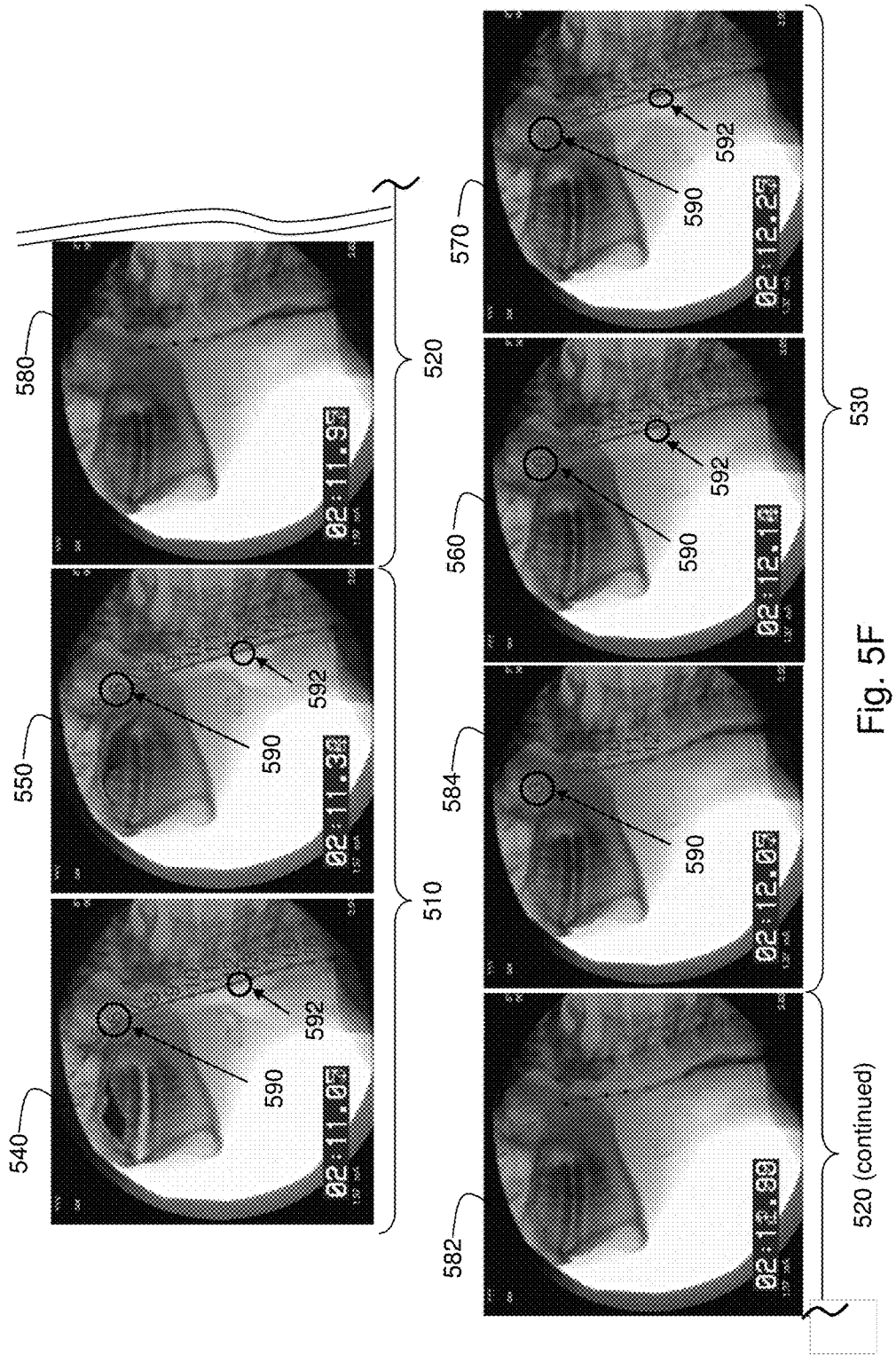
Figure 5G:
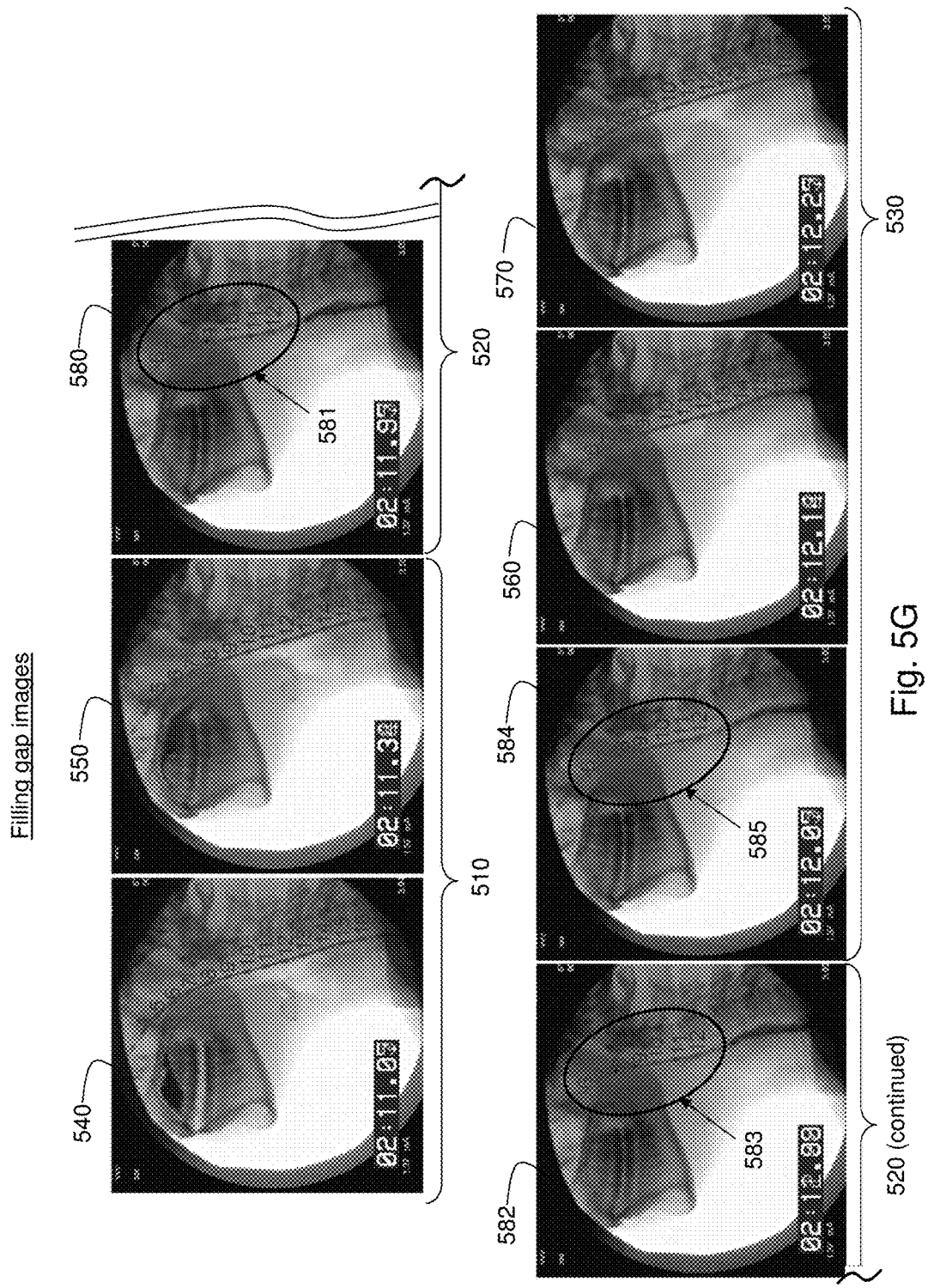

FIG. 5F demonstrates inter group synchronization, or adjustment, between sensor numbers in different groups of good images. Numbering/indexing of sensor locations in various images may be synchronized or adjusted (e.g., sensor locations may be serially renumbered) in terms of real, or genuine, sensor numbering/indexing/indexing within the involved/imaged sensing element. That is, during inter-groups synchronization, sensor locations in images may be serially renumbered (if an adjustment is required) such that a same index/serial number in different images indicates, identifies, represents, or is associated with, or corresponds/refers to the same sensor in the imaged sensing element. For example, after certain synchronization/adjustment is performed, all sensor locations numbered six (6) (these sensor locations are shown, in this example, at 590 in images 540, 550, 584, 560 and 570) refer to or represent the same sensor in the sensing element. The synchronization, or adjustment, process may be performed based, for example, on detection of a radiopaque marker or fiducial indicia (e.g., marker/fiducial indicia 592 in FIG. 5F) that may be built into, imbedded in, or added to, the sensing element. Detection of the marker, or fiducial indicia, may be performed for each group of good images separately. After the inter groups synchronization/adjustment process is completed, bad images in the images gap (e.g., bad images 580 and 582, FIG. 5F) may be filled with missing sensor locations as demonstrated, for example, in FIG. 5G. In FIG. 5G, sensor locations 6-12 are added to images 580, 582 and 584 (the added sensor locations 6-12 are respectively shown at 581, 583 and 585) using, for example, the method described in connection with FIG. 3A.

Figure 5H:
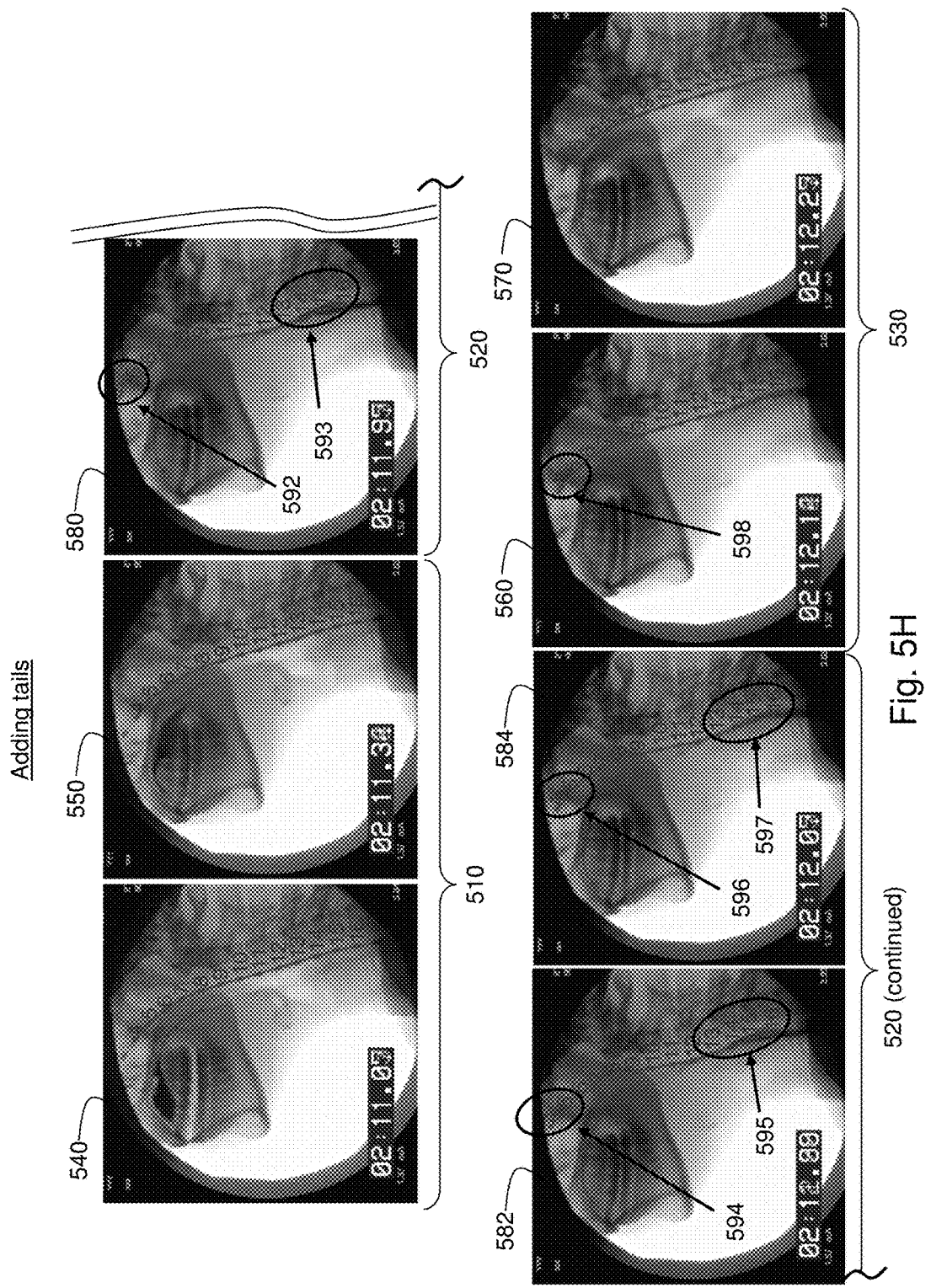

In FIG. 5H, 'heads' ('heading' sensor locations) and 'tails' ('tailing' sensor locations) in the images of the sensing element may be filled in or added to, for example, in image 580 (head 592 and tail 593), in image 582 (head 594 and tail 595), in image 584 (head 596 and tail 597) and in image 560 (head 598). Filling in missing heading sensor locations and tailing sensor locations may be performed, for example, by using the already estimated sensor locations, local sensor information, global sensor information, interpolation, etc. Adding heads and tails may be done by, for example, using the inter frame interpolation method described, for example, in connection with steps 4180-4190 of FIG. 4. Like the process used to estimate sensor locations in radiographic images, the process of filling in a sensor location in a radiographic image may include altering the radiographic image, or superimposing an image or a graphical object on the radiographic image, such that the location of a/the graphical object visually indicates or represents the location of the sensor in the radiographic image, whose location is filled in.

The embodiments described herein may include additional steps or phases. For example, in a preparation phase A0, which may be applied to swallow sequences on individual basis, a user operating an imaging/visualization system (e.g., system 100, FIG. 1A) may identify, mark or determine (or this step may be performed automatically, for example by a controller or processor) regions of interest (ROIs) in a stream of radiographic images. (A region of interest in an image may include a portion or an area of the image where a search for sensor location(s) is to be performed). The user may also identify or determine (or it may also be performed automatically by a controller/processor) portions of a stream of radiographic images associated with single-swallow sequences, to, thereby, partition an image stream into individual swallow sequences.

Preparation phase A0 may include another step, which is a semi-automatic estimation, or calculation of 'Distance-BeetweenSensors-to-pixels' scale. The shape and size of the physical sensors are known a priori. Therefore, a Distance-BeetweenSensors-to-pixels scale can be used (e.g., by the user or by a controller/processor) to visually determine or deduce the appearance of discernible sensors in radiographic images. To initiate the semi-automatic estimation a person may, by looking at the radiographic image, mark the centers of adjacent visible sensors (e.g., by using a mouse or another suitable user input device) providing initial estimation of DistanceBeetweenSensors-to-pixels scale. (The person may obviously select a high quality image in which the sensors are seen well, that is, in which sensors are clearly visible.)

The initial estimation can be used to form or create an initial pattern for discernible sensors' appearance. A software application, or an algorithm, may, then, use the initial pattern of discernible sensors to adjust the sensor center locations previously marked by the user. This kind of adjustment improves the accuracy of the Distance-BeetweenSensors-to-pixels scale estimation. The adjustment step can be repeated to further improve the Distance-BeetweenSensors-to-pixels scale estimation. The scale estimation may be improved further by using more than one pair of discernible adjacent sensors. Using Distance-BeetweenSensors-to-pixels scale estimation enables forming or generating a reference dark rectangle on bright background, as representative sensor image, which can be used to search for sensors in every image. That is, if a black spot/area in a radiographic image resembles the reference dark rectangle, the black spot/area may pictorially be regarded as a candidate sensor or sensor location.

A next stage or phase A1 of sensor localization algorithm/procedure may be applied to individual swallow sequences. The user, or a processor (by using an algorithm), may compare each area in each image to the reference dark rectangle to estimate similarity, and may select the areas in each image, which highly or best resemble the reference black rectangle. Then, a search for "local maxima" may be performed in order to find spots/areas that can be regarded as candidates for sensors or sensor locations. A classifier may be used to score each sensor candidate, and the, for example, 20% of the sensor candidates having the highest score values may finally be selected for further processing. Then, the sensors identification process applied to an image may be concluded by selecting the spots/areas in the image, whose inter sensors' distances and orientations 'make sense' or are 'reasonable' or acceptable (e.g., resemble a shape/contour of a sensor, with expected distances between them). These spots/areas may then be associatively "chained together".

After sensors are identified/detected and chained in the streamed images of a single swallow, images may be grouped into groups of good images and into group(s) of bad images. This grouping process may commence by searching for images that, for example, show, display or pictorially include long series or chains, of sensors, in the imaged sensing element (e.g., sensing element 112, FIG. 1A). Determination whether an image belongs to a group of good images (e.g., whether it can be classified as a good image) or to a group of bad images (e.g., whether it is to be classified as a bad image) may be done by counting (e.g., by a processor or a person) the number of discernible sensors in each image, and comparing this number, for example, to a threshold value. For example, the following criterion may be used to classify images (other criteria or formulae may be used):

$$Li \geq Max(0.5*L_{max}, X)$$

where Li is the number, L, of visible 'chained' sensors in image Bi, $L_{max}$ is the maximum number of sensors (e.g., the longest sensor chain) detected in an image (e.g., in any image of the image stream), and X is a fixed, predefined, default number (e.g., X=6). For example, assume that the default number of sensors, X, is equal to six (X=6). Also assume that, among the stream of images, image number ten depicts the greatest number of detected chained sensors, which, for the sake of the example, is eight ($L_{max}$=8). Continuing the example, since 0.5*8=4 and four is less than six (six being the example default value), any image for which the number of detected sensors, Li, is equal to or greater than six (Li≥Max{4,6}) is, according to this example, regarded as a "good" image, whereas any image for which the number of detected sensors, Li, is less than six is, according to the example regarded as a "bad" image.

Some embodiments may include estimating sensor locations in radiographic images, by for example: radiographically imaging a body organ containing a plurality of radiopaque sensors to provide a series of images (e.g., image series 200 in FIG. 2A, or series 500 in FIG. 5A) including a first group (e.g., image group 250 in FIG. 2A, or image group 510 in FIG. 5A) and second group (e.g., image group 270 in FIG. 2A, or image group 530 in FIG. 5A) of chronologically captured images and a third group (e.g., image group 260 in FIG. 2A, or image group 520 in FIG. 5A) of chronologically captured images chronologically interposed between the first group and second group of images, each image of the first and second groups of images (e.g., comprising a number of discernible sensors that is equal to or greater than a threshold number, each image of the third group of images comprising a number of discernible sensors that is less than the threshold number. Embodiments may include estimating sensor locations in images in the first and second groups of images, wherein the estimating includes performing, separately in/for each group, (i) reconstructing sensor locations of discernible sensors, and (ii) determining sensor locations of indiscernible sensors based on reconstructed locations of the discernable sensors, for example as per FIGS. 5A-5D. (Sensor locations of discernible sensors may be reconstructed, for example, using, or based, on visual similarity to a reference sensor appearance/image and visual similarity of objects between adjacent frames.)

Embodiments may additionally include estimating sensor locations in images of the third group of images (e.g., image group 260, or image group 530) by using estimated sensor locations in an image of the first group of images and in an image of the second group of images, and estimating additional sensor locations in images of the entire series (200, 500) of images based on the sensor locations estimated in the first, second and third image groups. A processor may be configured to perform all the methods, steps, calculations, counting, reconstructions, estimations, determinations steps/processes described herein, or only some of them (e.g., tasks may be distributed among several processors/controllers).

The articles "a" and "an" are used herein to refer to one or to more than one (e.g., to at least one) of the grammatical object of the article, depending on the context. By way of example, depending on the context, "an element" can mean one element or more than one element. The term "including" is used herein to mean, and is used interchangeably with, the phrase "including but not limited to". The terms "or" and "and" are used herein to mean, and are used interchangeably with, the term "and/or," unless context clearly indicates otherwise. The term "such as" is used herein to mean, and is used interchangeably, with the phrase "such as but not limited to".

Different embodiments are disclosed herein. Features of certain embodiments may be combined with features of other embodiments; thus certain embodiments may be combinations of features of other or multiple embodiments. Embodiments of the invention may include an article such as a computer or processor non-transitory storage medium, such as for example a memory, a disk drive, or a USB flash memory, encoding, including or storing instructions, e.g., computer-executable instructions, which when executed by a processor or controller, carry out methods disclosed herein. For example, a system may include a non-transitory storage medium such as storage unit 172, computer-executable instructions and a controller such as controller/processor 140 or 170. Some embodiments may be provided in a computer program product that may include a non-transitory machine-readable medium, having stored thereon instructions, which may be used to program a computer, or other programmable devices, to perform methods as disclosed above. Having thus described exemplary embodiments of the invention, it will be apparent to those skilled in the art that modifications of the disclosed embodiments will be within the scope of the invention. Alternative embodiments may, accordingly, include more modules, fewer modules and/or functionally equivalent modules. The present disclosure is relevant to various types of imaging systems (e.g., fluoroscopic/radiographic imaging systems, etc.) and to various types of sensors. Hence the scope of the claims that follow is not limited by the disclosure herein.

The invention claimed is:

1. A method for estimating sensor locations in radiographic images, comprising:
   radiographically imaging a body organ containing a plurality of radiopaque sensors to provide a series of images comprising a first and second groups of chronologically captured images and a third group of chronologically captured images chronologically interposed between the first and second groups of images, each image of the first and second groups of images comprising a number of discernible sensors that is equal to or greater than a threshold number, each image of the third group of images comprising a number of discernible sensors that is less than the threshold number;
   estimating sensor locations in images in the first and second groups of images, the estimating comprising, separately in each group,
      (i) reconstructing sensor locations of discernible sensors, and
      (ii) determining sensor locations of indiscernible sensors based on the reconstructed locations of the discernable sensors;
   estimating sensor locations in images of the third group of images using estimated sensor locations in an image of the first group of images and in an image of the second group of images; and
   estimating additional sensor locations in images of the entire series of images based on the sensor locations estimated in the first, second and third image groups.

2. The method as in claim 1, wherein the first group of images comprises images captured before a contrast material is administered into the body organ, the third group of images comprises images captured while the contrast material moves in the body organ, and the second group of images comprises images captured after the contrast material is cleared from the body organ.

3. The method as in claim 2, wherein administration of the contrast material into the body organ is performed by swallowing, and wherein the body organ is the esophagus.

4. The method as in claim 1, comprising:
   initially numbering reconstructed discernible sensor locations within each image within each of the first and second groups of images regardless of other images;
   intra synchronizing sensor numbers internally in each of the first and second groups of images, the synchronization comprising serially, and independently for each group, renumbering reconstructed discernible sensor locations within each of the first and second image groups such that a same number within all images of the first group refers to the same imaged sensor and a same number within all images of the second group refers to the same imaged sensor;
   enhancing sensor locations within each of the first and second image groups, the enhancement comprising, for each particular image group, estimating location of additional sensors in any image of the particular group based on sensor locations of discernable sensors already reconstructed in other images of the same particular group; and
   enlarging the first group and the second group of images by improving sensor estimation results in the images of third group of images adjacent to either the first or the second groups of images.

5. The method as in claim 1, wherein estimating the sensor locations in images of the third group of images comprising:
   inter synchronizing numbering of sensor locations across or between the first and second image groups, the synchronization comprising renumbering of sensor locations in images such that a same number in all images of the first and second groups of images refers to the same imaged sensor; and
   estimating sensor locations for both discernible and indiscernible sensors in the third group of images.

6. The method as in claim 5, wherein the third group of images comprises n chronologically captured images, B1, . . . , Bn, and wherein estimating the sensor locations for sensors in the third group of images comprises:
   determining a first set of candidate sensor locations in image B1 from sensor locations in an image of the first group of images and, starting from i=1, determining, iteratively, a first set of candidate sensor locations in image Bi+1, until a first set of candidate sensor locations is determined in image Bn;
   determining a second set of candidate sensor locations in image Bn from sensor locations in an image of the second group of images and, starting from i=n, determining, iteratively, a second set of candidate sensor locations in image Bi−1, until a second set of candidate sensor locations is determined in image B1; and
   estimating sensor locations in each image Bi of images B1, . . . , Bn using the pertinent first and second sets of candidate sensor locations.

7. The method as in claim 6, wherein the image of the first group of images used to determine the first set of candidate sensor locations in image B1 is the last chronological image in the first group of images, and wherein the image of the second group of images used to determine the second set of candidate sensor locations in image Bn is the first chronological image in the second group of images.

8. The method as in claim 6, wherein image B1 is chronologically subsequent to the last image of the first group of images and image Bn chronologically precedes the first image of the second group of images.

9. The method as in claim 6, wherein iteratively determining the first set of candidate sensor locations for image Bi+1 comprises using the first set of sensor locations estimated for image Bi, and wherein iteratively determining the second set of candidate sensor locations for image Bi−1 comprises using the second set of sensor locations estimated for image Bi.

10. The method as in claim 6, wherein estimating a particular sensor location in a particular image Bi comprises:
   (i) determining consistency between a first candidate sensor location determined for the sensor in image Bi, and a second candidate sensor location determined for the sensor in image Bi; and (ii) if the two determined candidate sensor locations are consistent within a predetermined margin, estimating the location of the sensor in image Bi from the two candidate sensor locations.

11. The method as in claim 10, comprising:
(iii) repeating steps (i) and (ii) for other sensors in the particular image Bi; and
(iv) repeating steps (i) and (iii) for other images Bi.

12. The method as in claim 10, comprising calculating, for each sensor, a consistency grade to determine positional consistency between the pertinent candidate sensor locations.

13. The method as in claim 1, wherein estimating the additional sensor locations in images of the entire series of images comprises:
(i) estimating locations of sensors in a particular image Bi based on sensor locations already estimated for other sensors in the same particular image Bi; and
(ii) estimating additional sensor locations in images of the first group, the second group and the third group of images based on inter-frame interpolation of already estimated sensor locations in the first group, the second group and the third group of images.

14. The method as in claim 1, comprising:
counting a number L of radiographically discernible sensors in images in the series of images; and
classifying an image as belonging to the first group of images or to the second group of images, or to the third group of images based on the pertinent L value.

15. The method as in claim 1, further comprising displaying sensor locations on a display device.

16. A method for estimating sensor locations in radiographic images, comprising:
receiving a series of chronologically captured radiopaque images, the series of images imaging a body organ containing a plurality of radiopaque sensors, the series of images comprising a first group and a second group of chronologically captured images, each image comprising a number of discernible sensors that is equal to or greater than a threshold number, and a third group of n chronologically captured images B1, . . . , Bn chronologically captured between the first and second groups of images, each image of the third group of images comprising a number of discernible sensors that is less than the threshold number;
reconstructing sensor locations of discernible sensors in the first and second groups of images;
determining sensor locations of indiscernible sensors in the first and second groups of images based on the reconstructed locations of the discernable sensors; and
estimating sensor locations in images of the third group of images using reconstructed and determined sensor locations in an image of the first group of images and in an image of the second group of images.

17. The method as in claim 16, further comprising estimating additional sensor locations in images of the entire series of images based on the sensor locations estimated in the first group of images, second group of images and third group of images.

18. A system for reconstructing sensor locations in radiographic images, comprising:
a processor configured to:
receive a series of chronologically captured radiopaque images, the series of images imaging a body organ containing a plurality of radiopaque sensors, the series of images comprising a first group and a second group of chronologically captured images, each image comprising a number of discernible sensors that is equal to or greater than a threshold number, and a third group of n chronologically captured images B1, . . . , Bn chronologically captured between the first and second groups of images, each image of the third group of images comprising a number of discernible sensors that is less than the threshold number;
estimate sensor locations in images in the first and second groups of images by performing, separately for each group,
(i) reconstructing sensor locations of discernible sensors, and
(ii) determining sensor locations of indiscernible sensors based on the reconstructed locations of the discernable sensors;
estimate sensor locations in images of the third group of images by using estimated sensor locations in an image of the first group of images and in an image of the second group of images; and
estimate additional sensor locations in images of the entire series of images based on the sensor locations estimated in the first, second and third image groups; and
a display device to display images with estimated sensor locations.

19. The system as in claim 18, wherein the processor is configured to:
initially number reconstructed discernible sensor locations within each image within each of the first and second groups of images regardless of other images;
intra synchronize sensor numbers internally in each of the first and second groups of images, by serially, and independently for each group, renumbering reconstructed discernible sensor locations within each of the first and second image groups such that a same number within all images of the first group refers to the same imaged sensor and a same number within all images of the second group refers to the same imaged sensor;
enhance sensor locations within each of the first and second image groups, by, for each particular image group, estimating location of additional sensors in any image of the particular group based on sensor locations of discernable sensors already reconstructed in other images of the same particular group; and
enlarge the first group and the second group of images by improving sensor estimation results in the third group of bad images adjacent to either the first or the second groups of images.

20. The system as in claim 18, wherein the processor is configured to estimate the sensor locations in images of the third group of images by:
inter synchronizing numbering of sensor locations across or between the first and second image groups, the synchronization comprising renumbering of sensor locations in images such that a same number in all images of the first and second groups of images refers to the same imaged sensor; and
estimating sensor locations for both discernible and indiscernible sensors in the third group of images.

21. The system as in claim 20, wherein the third group of images comprises n chronologically captured images, B1, . . . , Bn, and wherein the processor is configured to estimate the sensor locations for sensors in the third group of images by:
determining a first set of candidate sensor locations in image B1 from sensor locations in an image of the first group of images and, starting from i=1, determining, iteratively, a first set of candidate sensor locations in image Bi+1, until a first set of candidate sensor locations is determined in image Bn;

determining a second set of candidate sensor locations in image Bn from sensor locations in an image of the second group of images and, starting from i=n, determining, iteratively, a second set of candidate sensor locations in image Bi−1, until a second set of candidate sensor locations is determined in image B1; and estimating sensor locations in each image Bi of images B1, . . . , Bn using the pertinent first and second sets of candidate sensor locations.

22. The system as in claim 18, wherein the processor is configured to classify an image as belonging to the first group of images or to the second group of images, or to the third group of images based on a number of radiographically discernible sensors in the image.

23. The system as in claim 18, further comprising an imaging system to provide the series of chronological radiopaque images.

* * * * *